(12) United States Patent
Bao et al.

(10) Patent No.: US 8,227,483 B2
(45) Date of Patent: Jul. 24, 2012

(54) POLYMORPHS OF 6-BETA-NALTREXOL

(75) Inventors: Jian Bao, Chesterfield, MO (US); Gary A. Nichols, Wildwood, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 439 days.

(21) Appl. No.: 12/563,295

(22) Filed: Sep. 21, 2009

(65) Prior Publication Data

US 2010/0076007 A1 Mar. 25, 2010

Related U.S. Application Data

(60) Provisional application No. 61/098,871, filed on Sep. 22, 2008.

(51) Int. Cl.
*A61K 31/485* (2006.01)
*C07D 489/08* (2006.01)

(52) U.S. Cl. ........................................ 514/282; 546/44

(58) Field of Classification Search .................. 514/282; 546/44

See application file for complete search history.

(56) References Cited

U.S. PATENT DOCUMENTS

| 4,089,855 A | 5/1978 | Chatterjie et al. |
| 2008/0008745 A1 | 1/2008 | Stinchcomb et al. |
| 2009/0017102 A1 | 1/2009 | Stinchcomb et al. |

OTHER PUBLICATIONS

Hamad et al.; "Synthesis and hydrolytic behavior of two novel tripartate codrugs of Naltrexone and . . . "; Bioorganic & Medicinal chemistry; 14(20); 2006; pp. 7051-7061; XP 002554717.
Hosztafi et al.; "Synthesis of N-Demethyl-N-Substituted . . . "; Heterocycles, 36(7); 1993, pp. 1509-1520; XP 002554718.

*Primary Examiner* — Charanjit Aulakh

(57) ABSTRACT

The present invention provides polymorphs of 6-beta-naltrexol and process for their preparation. In particular, the present invention provides crystalline forms of the free base of 6-beta-naltrexol and processes for their preparation. The present invention also provides crystalline and amorphous forms of the hydrochloride salt of 6-beta-naltrexol and processes for their preparation.

7 Claims, 14 Drawing Sheets

POLYMORPHS OF 6-BETA-NALTREXOL

CROSS REFERENCE TO RELATED APPLICATIONS

This application claims the benefit of the filing date of U.S. Provisional Application Serial no. 61/098,871, filed Sep. 2, 2008, entitled "Polymorphs of 6-Beta-Naltrexol" which is incorporated herein in their entirety.

FIELD OF THE INVENTION

The present invention generally relates to polymorphs of 6-beta-naltrexol and processes for their preparation. In particular, the invention relates to crystalline forms of 6-beta-naltrexol base, as well as crystalline and amorphous forms of 6-beta-naltrexol hydrochloride.

BACKGROUND OF THE INVENTION

Substance dependency is a prevalent disease both domestically and abroad, with substantial morbidity and mortality associated with the disease state. Typically detoxification and psychosocial therapy are the primary treatments, however, pharmaceutical treatment has gained acceptance as a feasible treatment alternative. One such treatment, naltrexone, a mu opioid receptor antagonist, is used in the treatment of opioid and alcohol dependence. Naltrexone's longer duration of action compared to naloxone (another pharmaceutical substance abuse treatment) has been considered to be due partly to its major human metabolite, 6-beta-naltrexol (i.e., morphinan-3,6,14-triol,17-(cyclopropylmethyl)-4,5-epoxy). The potency of 6-beta-naltrexol in vivo is time-dependent, and it has a longer duration of action than naloxone and naltrexone, consistent with a longer pharmacokinetic terminal half-life.

Beyond their use to treat substance dependency, opioid antagonists have also been shown to be useful in the treatment of pruritis associated with liver disease or opioid medications. However, despite a wide range of clinical applications, the primary disadvantages of treatment with an opioid antagonist such as naltrexone or naloxone, is the possibility of inducing withdrawal, due to the receptor blocking qualities of the therapeutic agents. Clinical trials have shown that treatment with 6-beta-naltrexol precipitated only minimal withdrawal at high doses in an acute dependence model and was approximately 77-and 30-fold less potent than naltrexone and naloxone, respectively, in precipitating withdrawal in a chronic dependence model. 6-Beta-naltrexol is available in both the base and hydrochloride salt forms of the medication. Drug delivery systems for 6-beta-naltrexol can include IV, oral, and trans-dermal methods, in which solubility is critical to all dosage forms. Despite its therapeutic uses, no polymorphs of 6-beta-naltrexol have been characterized.

Solids exist in either amorphous or crystalline forms. In the case of crystalline forms, molecules are positioned in three-dimensional lattice sites. When a compound recrystallizes from a solution or slurry, it may crystallize with different spatial lattice arrangements, and the different crystalline forms are sometimes referred to as "polymorphs." The different crystalline forms of a given substance may differ from each other with respect to one or more chemical properties (e.g., dissolution rate, solubility), biological properties (e.g., bioavailability, pharmacokinetics), and/or physical properties (e.g., mechanical strength, compaction behavior, flow properties, particle size, shape, melting point, degree of hydration or salvation, caking tendency, compatibility with excipients). The variation in properties among different crystalline forms usually means that one crystalline form is desired or preferred over other forms.

Because 6-beta-naltrexol exhibits several advantageous therapeutic properties, such as a longer half-life, and decreased likelihood of inducing withdrawal, improved forms of the compound are desired, particularly with regard to enhanced solubility, bioavailability, ease of synthesis, ability to be readily formulated, and/or physical stability. Thus, there is a need for improved crystalline forms of 6-beta-naltrexol and methods for preparing the different forms.

SUMMARY OF THE INVENTION

The present invention provides two crystalline forms of the free base of 6-beta-naltrexol, as well as processes for their preparation. The present invention also provides eleven crystalline forms and one amorphous form of the hydrochloride salt of 6-beta-naltrexol, as well as processes for their preparation.

One aspect of the invention encompasses a crystalline form of 6-beta-naltrexol base, morphinan-3,6,14-triol,17-(cyclopropylmethyl)-4,5-epoxy, wherein the crystalline form is selected from the group consisting of Form $I_B$ and Form $II_B$.

Another aspect of the invention provides a polymorph of 6-beta-naltrexol hydrochloride, morphinan-3,6,14-triol,17-(cyclopropylmethyl)-4,5-epoxy, wherein the polymorph is selected from the group consisting of crystalline Form $I_S$, crystalline Form $II_S$, crystalline Form $III_S$, crystalline Form $IV_S$, crystalline Form $V_S$, crystalline Form $VI_S$, crystalline Form $VII_S$, crystalline Form $VIII_S$, crystalline Form $IX_S$, crystalline Form $X_S$, crystalline Form $XI_S$, and an amorphous form.

A further aspect of the invention provides a pharmaceutical composition comprising at least one crystalline form of 6-beta-naltrexol base, morphinan-3,6,14-triol,17-(cyclopropylmethyl)-4,5-epoxy, and at least one pharmaceutically acceptable excipient, wherein the crystalline form of 6-beta-naltrexol base is selected from the group consisting of Form $I_B$, Form $II_B$, and combinations thereof.

Still aspect of the invention encompasses a pharmaceutical composition comprising at least one polymorph of 6-beta-naltrexol hydrochloride, morphinan-3,6,14-triol,17-(cyclopropylmethyl)-4,5-epoxy, and at least one pharmaceutically acceptable excipient, wherein the polymorph of 6-beta-naltrexol hydrochloride is selected from the group consisting of crystalline Form $I_S$, crystalline Form $II_S$, crystalline Form $III_S$, crystalline Form $IV_S$, crystalline Form $V_S$, crystalline Form $VI_S$, crystalline Form $VII_S$, crystalline Form $VIII_S$, crystalline Form $IX_S$, crystalline Form $X_S$, crystalline Form $XI_S$, an amorphous form, and combinations thereof.

Yet another aspect of the invention provides a process for preparing a substantially pure crystalline form of 6-beta-naltrexol base, morphinan-3,6,14-triol,17-(cyclopropylmethyl)-4,5-epoxy. The process comprises contacting 6-beta-naltrexol base with a solvent to form a saturated or a near saturated solution and forming crystals of the substantially pure crystalline form of 6-beta-naltrexol base.

A further aspect of the invention provides a process for preparing a substantially pure crystalline form of 6-beta-naltrexol hydrochloride, morphinan-3,6,14-triol,17-(cyclopropylmethyl)-4,5-epoxy. The process comprises contacting 6-beta-naltrexol hydrochloride with a solvent to form a saturated or a near saturated solution and forming crystals of the substantially pure crystalline form of 6-beta-naltrexol hydrochloride.

Another aspect of the invention encompasses a process for preparing a substantially pure amorphous form of 6-betanaltrexol hydrochloride, morphinan-3,6,14-triol,17-(cyclopropylmethyl)-4,5-epoxy. The process comprises contacting 6-beta-naltrexol hydrochloride with a solvent to form a saturated or near saturated solution and evaporating the solvent to form the substantially pure amorphous form of 6-beta-naltrexol hydrochloride.

Other aspects and features of the invention will be in part apparent and in part described in more detail below.

DETAILED DESCRIPTION

Figure 1:
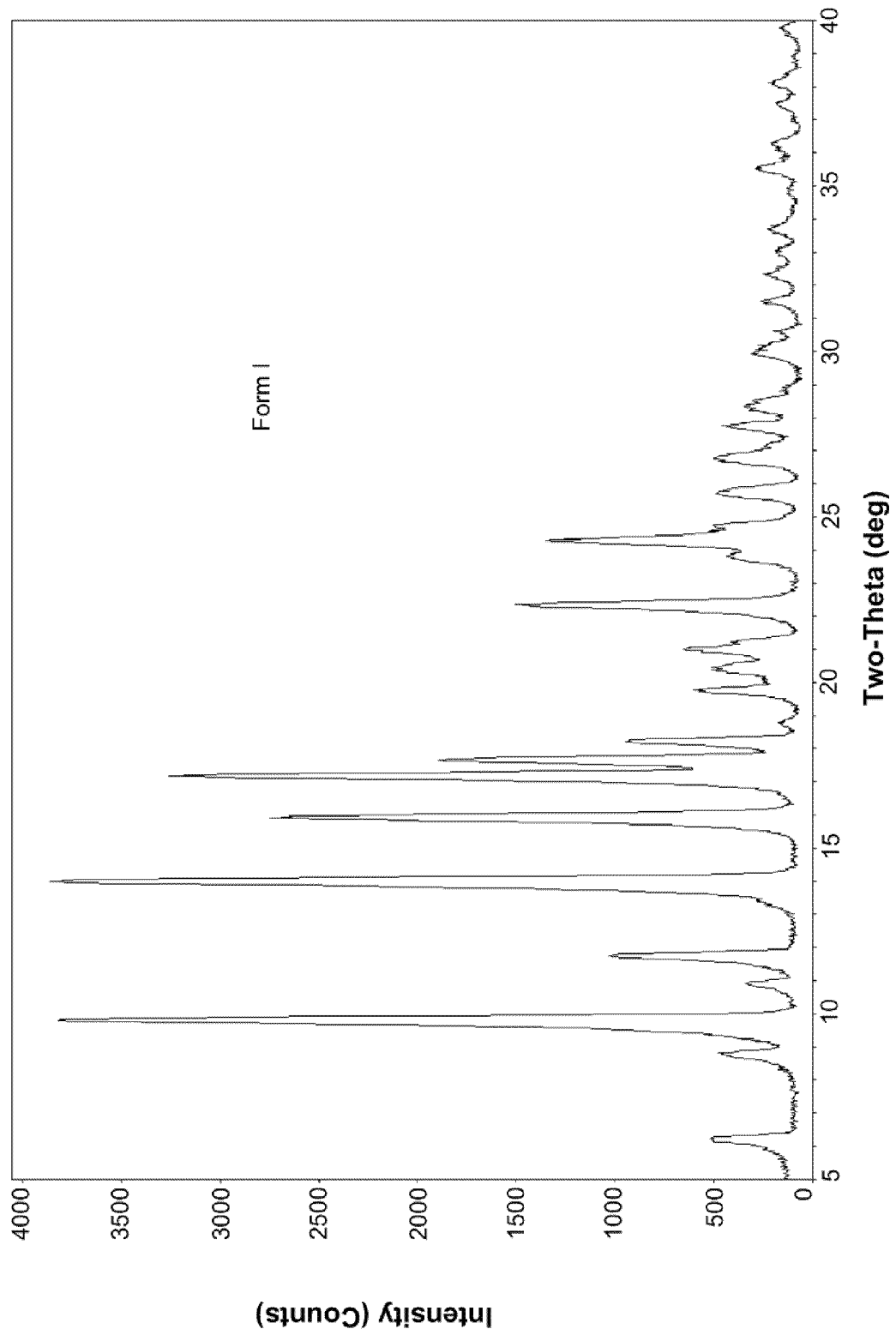
FIG. 1 represents an X-ray powder diffraction pattern of crystalline Form I of 6-beta-naltrexol base. Peak intensity is plotted as a function of degrees 2-theta.

It has been discovered that the free base and the hydrochloride salt of 6-beta-naltrexol may exist as any of several polymorphs. The polymorphs differ from each other with respect to their physical properties, spectral data, stability, and methods of preparation. Two crystalline forms of 6-beta-naltrexol base are described herein, and are hereinafter referred to, respectively, as Form $I_B$ and Form $II_B$. Eleven crystalline forms of the hydrochloride salt of 6-beta-naltrexol are described herein, and are hereinafter referred to, respectively, as Form $I_S$, Form $II_S$, Form $III_S$, Form $IV_S$, Form $V_S$, Form $VI_S$, Form $VII_S$, Form $VIII_S$, Form $IX_S$, Form $X_S$, and Form $XI_S$. Additionally, an amorphous form of 6-beta-naltrexol hydrochlorides is also described herein. The present invention also provides pharmaceutical compositions comprising at least one the polymorphs of 6-beta-naltrexol. Also provided are processes for producing the different polymorphs of 6-beta-naltrexol.

(I) Crystalline Forms of 6-Beta-Naltrexol Base

A first aspect of the invention encompasses polymorphs of the free base of 6-beta-naltrexol. Solid crystalline 6-beta-naltrexol base may exist in two different crystalline forms. The two crystalline forms may be distinguished on the basis of different X-ray powder diffraction patterns, different endotherms and/or exotherms, as determined by differential scanning calorimetry, as well as different thermogravimetric analysis profiles. Those of skill in the art will appreciate that other analytical techniques, such as single crystal X-ray diffraction analysis, water vapor sorption, Fourier transform infrared spectroscopy, etc., also may be used to differentiate the two different crystalline forms.

In one embodiment, crystalline 6-beta-naltrexol base may exist as monohydrous Form $I_B$. Crystalline Form $I_B$ exhibits an X-ray powder diffraction pattern comprising characteristic peaks expressed in degrees 2-theta as diagrammed in FIG. 1. In particular, Form $I_B$ exhibits diffraction peaks at 6.240, 8.838, 9.820, 10.920, 11.780, 14.001, 15.941, 17.200, 17.680, 18.240, 18.818, 19.781, 20.460, 21.021, 21.259, 22.379, 23.839, 24.299, 24.759, 25.721, 26.781, 27.760, 28.360, 28.935, 29.941, 30.639, 31.541, 32.341, 33.082, 33.718, 35.540, 36.298, 37.518, and 38.139 degree 2-theta. More specifically, Form $I_B$ has predominant peaks at about 9.8, about 14.0, about 15.9, about 17.2, about 17.7, and about 22.4 degrees 2-theta (±0.15 degrees 2-theta). Form $I_8$ exhibits a differential scanning calorimetry profile having an endotherm/exotherm from about 75°-125° C. and an endotherm at about 185°-190° C. Form $I_B$ also exhibits a thermogravimetric analysis showing a loss of mass of about 4.0-6.0% from about 75°-160° C.

In another embodiment, crystalline 6-beta-naltrexol base may also exist as anhydrous Form $II_B$. This crystalline form exhibits an X-ray powder diffraction pattern comprising characteristic peaks expressed in degrees 2-theta as diagrammed in FIG. 2. In particular, Form $II_B$ exhibits peaks at 7.098, 9.381, 9.859, 10.900, 12.060, 12.539, 13.041, 14.120, 14.842, 15.221, 15.560, 16.542, 17.182, 18.081, 18.661, 19.061, 20.499, 21.042, 21.843, 22.219, 22.900, 23.660, 24.121, 25.200, 25.800, 26.300, 27.359, 28.642, 30.558, 31.359, 31.920, 34.257, 35.704, and 37.678 degrees 2-theta. Specifically, Form $II_B$ exhibits predominant peaks at about 10.9, about 15.6, about 16.5, about 17.2, and about 18.7 (±0.15 degrees 2-theta). Form $II_B$ exhibits a differential scanning calorimetry profile having an endotherm/exotherm from 90-110° C., and an endotherm at about 189-190° C. Form $II_B$ also exhibits a thermogravimetric analysis showing a loss of mass of about 0.2-0.3% from about 75-125° C.

(II) Polymorphs of 6-Beta-Naltrexol Hydrochloride

Another aspect of the invention encompasses polymorphs of the hydrochloride salt of 6-beta-naltrexol. Solid 6-beta-naltrexol hydrochloride may exist as any of eleven crystalline forms or one amorphous form. The twelve polymorphs may be distinguished on the basis of different X-ray powder diffraction patterns or simulated X-ray powder diffraction patterns (i.e., calculated from single crystal X-ray data), different endotherms and/or exotherms as determined by differential scanning calorimetry, and different thermogravimetric analyses. Those of skill in the art will appreciate that other analytical techniques may be used to differentiate the different polymorphs.

In one embodiment, solid 6-beta-naltrexol hydrochloride may exist as anhydrous crystalline Form $I_S$. Crystalline Form $I_S$ of 6-beta-naltrexol hydrochloride exhibits an X-ray powder diffraction pattern comprising characteristic peaks expressed in degrees 2-theta as diagrammed in FIG. 3. Form $I_S$ exhibits peaks at 10.739, 12.101, 12.821, 13.321, 13.939, 15.943, 16.860, 17.182, 17.880, 18.938, 19.822, 20.101, 21.181, 21.682, 22.659, 23.339, 24.180, 24.680, 25.464, 26.843, 27.656, 27.997, 29.162, 29.498, 30.015, 30.982, 31.399, 32.301, 33.081, 33.798, 34.340, 35.441, 35.920, 37.216, and 39.320 degrees 2-theta. In particular, Form $I_S$ exhibits predominant peaks at about 12.8, about 13.9, about 22.7, about 23.3, and about 24.2 degrees 2-theta (±0.15 degrees 2-theta). Form $I_S$ of 6-beta-naltrexol hydrochloride exhibits an endotherm from about 40°-100° C. and an exotherm/endotherm above about 190° C., as measured by differential scanning calorimetry. Crystalline Form $I_S$ of 6-beta-naltrexol hydrochloride exhibits a loss of mass of about 0.2-0.3% from about 40°-100° C., as measured by thermogravimetric analysis.

In another embodiment, solid 6-beta-naltrexol hydrochloride may exist as hydrous crystalline Form $II_S$. Crystalline Form $II_S$ of 6-beta-naltrexol hydrochloride exhibits an X-ray powder diffraction pattern comprising characteristic peaks expressed in degrees 2-theta as diagrammed in FIG. 4. In particular, Form $II_S$ has peaks at 7.398, 9.399, 11.019, 11.922, 12.378, 13.219, 14.859, 15.582, 16.003, 16.462, 16.700, 18.002, 18.761, 19.499, 21.340, 21.720, 22.498, 23.120, 24.001, 24.682, 25.080, 26.003, 26.499, 27.002, 28.002, 28.481, 28.962, 29.579, 30.197, 30.761, 31.419, 31.983, 32.462, 33.021, 35.181, 35.750, 36.678, 37.282, and 38.909 degrees 2-theta. More particularly, Form $II_S$ had predominant peaks at about 7.4, about 11.0, about 11.9, about 14.9, about 15.6, and about 18.8 degrees 2-theta (±0.15 degrees 2-theta).

In a further embodiment, solid 6-beta-naltrexol hydrochloride may exist as anhydrous or dihydrous crystalline Form $III_S$. Crystalline Form $III_S$ of 6-beta-naltrexol hydrochloride exhibits an X-ray powder diffraction pattern comprising characteristic peaks expressed in degrees 2-theta as diagrammed in FIG. 5. Form $III_S$ has peaks at 10.581, 12.279, 13.300, 13.721, 16.022, 16.861, 17.180, 18.899, 19.800, 20.962, 21.261, 22.160, 22.542, 23.200, 23.792, 24.718, 25.477, 26.202, 26.781, 27.095, 27.577, 28.021, 28.362, 28.537, 29.046, 29.402, 30.020, 30.637, 30.924, 31.281, 32.279, 32.698, 33.577, 34.120, 34.498, 35.253, 35.702, 36.359, 37.144, 37.462, 37.901, 38.458, 38.844, and 39.377 degrees 2-theta. In particular, Form $III_S$ has predominant peaks at about 12.3, about 13.3, about 21.3, about 22.5, about 24.7, and about 38.8 degrees 2-theta (±0.15 degrees 2-theta). Form $II_S$ of 6-beta-naltrexol hydrochloride exhibits a first endotherm from about 25°-125° C. and a second endotherm above about 175° C., as measured by differential scanning calorimetry. Crystalline Form $II_S$ of 6-beta-naltrexol hydrochloride exhibits a loss of mass of about 7.0-9.0% from about 25°-125° C., as measured by thermogravimetric analysis.

In still another embodiment, solid 6-beta-naltrexol hydrochloride may exist as crystalline Form $IV_S$, which is an ethyl alcohol solvate. Crystalline Form $IV_S$ of 6-beta-naltrexol hydrochloride exhibits an X-ray powder diffraction pattern comprising characteristic peaks expressed in degrees 2-theta as diagrammed in FIG. 6. This form has peaks at 10.118, 11.523, 12.820, 14.017, 15.275, 16.240, 17.160, 18.518, 19.924, 20.341, 20.823, 21.001, 21.452, 22.258, 22.982, 23.380, 23.918, 24.643, 25.080, 25.921, 26.340, 26.720, 27.079, 28.201, 28.919, 29.297, 30.718, 31.082, 31.624, 32.381, 32.899, 33.899, 34.774, 35.120, 36.258, 36.663, 37.239, 39.084, and 39.354 degrees 2-theta. In particular, Form $IV_S$ has predominant peaks at about 11.5, about 12.8, about 18.5, about 22.3, about 23.0, and about 23.9 degrees 2-theta (±0.15 degrees 2-theta). Form $IV_S$ of 6-beta-naltrexol hydrochloride exhibits an endotherm from about 150°-200° C., as measured by differential scanning calorimetry. Crystalline Form $IV_S$ of 6-beta-naltrexol hydrochloride shows a loss of mass of about 6.0-12.0% from about 150°-200° C., as measured by thermogravimetric analysis In an alternate embodiment, solid 6-beta-naltrexol hydrochloride may exist as crystalline Form $V_S$, which is an acetonitrile solvate. Crystalline Form $V_S$ of 6-beta-naltrexol hydrochloride exhibits an X-ray powder diffraction pattern comprising characteristic peaks expressed in degrees 2-theta as diagrammed in FIG. 7. This form displays peaks at 7.261, 7.759, 9.420, 9.938, 11.600, 12.163, 12.681, 13.583, 14.903, 15.580, 16.065, 16.399, 17.138, 18.599, 19.198, 19.822, 20.686, 22.143, 22.822, 23.299, 23.702, 24.544, 25.282, 25.660, 26.020, 26.679, 27.098, 27.664, 28.000, 28.519, 29.359, 29.626, 30.000, 30.897, 32.641, 34.320, 34.896, 35.718, 36.497, 36.844, 37.498, 38.360, and 38.959 degrees 2-theta. In particular, Form $V_S$ exhibits predominant peaks at about 7.8, about 12.7, about 13.6, about 16.1, about 19.8, and about 23.7 degrees 2-theta (±0.15 degrees 2-theta). Form $V_S$ of 6-beta-naltrexol hydrochloride exhibits an endotherm from about 100°-150° C. and an endotherm/exotherm from about 175°-200° C., as measured by differential scanning calorimetry. Crystalline Form $V_S$ of 6-beta-naltrexol hydrochloride exhibits a first loss of mass of about 1.0-1.5% from about 75°-125° C. and a second loss of mass of about 8.0-9.0% from about 150°-180° C., as measured by thermogravimetric analysis.

In another embodiment, solid 6-beta-naltrexol hydrochloride may exist as crystalline Form $VI_S$, which is an isopropyl alcohol solvate. Crystalline Form $VI_S$ of 6-beta-naltrexol hydrochloride exhibits an X-ray powder diffraction pattern comprising characteristic peaks expressed in degrees 2-theta as diagrammed in FIG. 8. This form exhibits peaks at 7.138, 7.538, 9.082, 9.658, 10.939, 12.240, 13.181, 14.361, 14.858, 15.262, 15.983, 16.239, 17.097, 18.301, 19.359, 19.921, 21.619, 21.980, 22.481, 22.699, 23.161, 23.439, 23.740, 24.340, 24.701, 24.955, 25.541, 25.800, 26.363, 26.859, 27.459, 28.020, 28.498, 28.938, 29.819, 30.040, 30.640, 30.885, 31.899, 32.342, 33.220, 34.501, 34.960, 35.566, 36.259, 37.181, 38.190, 38.579, and 39.281 degrees 2-theta. In particular, Form $VI_S$ has predominant peaks at about 9.7, about 12.2, about 14.4, about 16.0, about 19.4, and about 19.9 degrees 2-theta (±0.15 degrees 2-theta). Form $VI_S$ of 6-beta-naltrexol hydrochloride exhibits an endotherm from about 150°-180° C. and an exotherm above about 180° C., as measured by differential scanning calorimetry. Crystalline Form $VI_S$ of 6-beta-naltrexol hydrochloride exhibits a first loss of mass of about 7.0-8.0% from about 150°-200° C. and a second loss of mass of about 1.0-2.0% from about 200°-225° C., as measured by thermogravimetric analysis.

In yet another embodiment, solid 6-beta-naltrexol hydrochloride may exist as crystalline Form $VII_S$, which is a methyl alcohol solvate. Crystalline Form $VII_S$ of 6-beta-naltrexol hydrochloride exhibits an X-ray powder diffraction pattern comprising characteristic peaks expressed in degrees 2-theta as diagrammed in FIG. 9. Form $VII_S$ exhibits peaks at 10.580, 12.021, 12.803, 13.084, 14.040, 15.520, 15.947, 16.457, 17.102, 18.538, 19.376, 20.021, 20.683, 21.383, 21.727, 22.369, 23.138, 23.459, 24.224, 24.443, 25.162, 26.202, 26.457, 27.383, 28.041, 28.224, 28.544, 29.418, 30.225, 30.820, 31.128, 32.410, 32.781, 34.335, 35.987, 36.479, 36.774, 37.371, 38.903, and 39.300 degrees 2-theta. This crystalline form has predominant peaks at about 12.0, about 13.1, about 21.4, about 22.4, and about 26.2 degrees 2-theta (±0.15 degrees 2-heta). Form VII$_S$ of 6-beta-naltrexol hydrochloride exhibits a first endotherm from about 50°-125° C. and a second endotherm from about 170°-200° C., as measured by differential scanning calorimetry. Crystalline Form VII$_S$ of 6-beta-naltrexol hydrochloride exhibits a first loss of mass of about 0.4-0.6% from about 75°-125° C. and a second loss of mass of about 7.0-8.0% from about 150°-200° C., as measured by thermogravimetric analysis.

In still another alternate embodiment, solid 6-beta-naltrexol hydrochloride may exist as crystalline Form VIII$_S$, which is an ethyl alcohol solvate. Crystalline Form VIII$_S$ of 6-beta-naltrexol hydrochloride exhibits an X-ray powder diffraction pattern comprising characteristic peaks expressed in degrees 2-theta as diagrammed in FIG. 10. Form VIII$_S$ displays peaks at 10.221, 11.480, 11.740, 12.862, 13.099, 14.097, 15.383, 16.461, 17.262, 17.958, 18.860, 20.082, 20.522, 20.920, 21.359, 21.562, 22.523, 23.258, 23.563, 24.361, 24.982, 25.319, 25.959, 26.362, 26.902, 27.502, 28.500, 28.763, 29.361, 30.761, 31.002, 31.262, 31.544, 31159, 32.102, 32.440, 33.140, 33.723, 34.240, 34.921, 35.820, 36.283, 36.962, 37.262, 37.681, 38.222, 38.643, 39.243, and 39.880 degrees 2-theta. In particular, Form VIII$_S$ has predominant peaks at about 11.7, about 12.9, about 13.1, about 18.9, and about 24.4 degrees 2-theta (±0.15 degrees 2-theta).

In a further embodiment, solid 6-beta-naltrexol hydrochloride may exist as crystalline Form IX$_S$, which is an isopropyl alcohol solvate. Crystalline Form IX$_S$ of 6-beta-naltrexol hydrochloride exhibits an X-ray powder diffraction pattern comprising characteristic peaks expressed in degrees 2-theta as diagrammed in FIG. 11. In particular, Form IX$_S$ has peaks at 7.419, 10.241, 10.741, 11.563, 11.902, 12.181, 13.303, 14.861, 15.422, 16.018, 16.260, 18.543, 19.159, 19.723, 20.561, 21.262, 21.843, 22.163, 22.821, 23.402, 24.019, 24.300, 25.000, 25.222, 25.801, 26.421, 26.784, 27.084, 27.621, 28.023, 28.621, 28.880, 29.443, 30.164, 31.561, 32.023, 32.582, 33.039, 33.938, 34.363, 34.842, 35.141, 35.640, 36.060, 36.819, 37.480, 37.778, 38.064, 38.540, and 38.862 degrees 2-theta. In particular, Form IX$_S$ exhibits predominant peaks at about 7.4, about 11.6, about 13.3, about 16.0, and about 16.3 degrees 2-theta (±0.15 degrees 2-theta).

Figure 12:
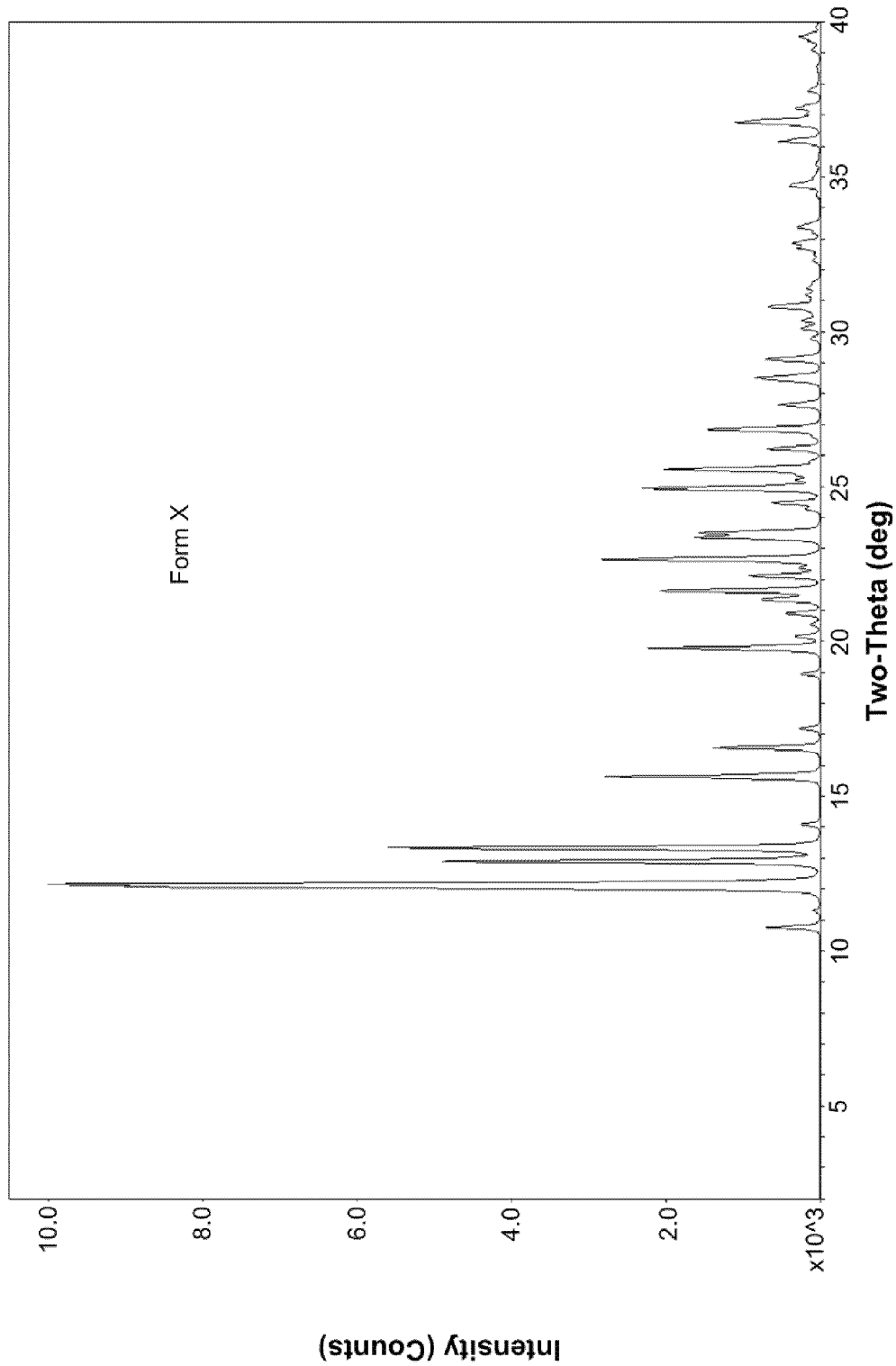
FIG. 12 represents an X-ray powder diffraction pattern simulated from single crystal X-ray diffraction data gathered from the analysis of crystalline Form X of 6-beta-naltrexol hydrochloride. Peak intensity is plotted as a function of degrees 2-theta.

In another alternate embodiment, solid 6-beta-naltrexol hydrochloride may exist as crystalline Form X$_S$, which is a methyl alcohol solvate. Crystalline Form X$_S$ of 6-beta-naltrexol hydrochloride exhibits an X-ray powder diffraction pattern comprising characteristic peaks expressed in degrees 2-theta as diagrammed in FIG. 12. Specifically, Form X$_S$ has peaks at 10.778, 11.318, 12.159, 12.903, 13.340, 14.100, 15.642, 16.579, 17.199, 18.959, 19.798, 20.163, 20.558, 20.902, 21.360, 21.641, 22.122, 22.659, 23.379, 24.282, 24.480, 24.943, 25.561, 26.222, 26.859, 27.641, 28.520, 29.119, 29.780, 30.120, 30.363, 30.819, 31.199, 31.403, 32.300, 32.861, 33.381, 34.440, 34.704, 35.401, 36.143, 36.761, 37.220, 37.782, 39.099, 39.521, and 39.821 degrees 2-theta. In particular, Form X$_S$ exhibits predominant peaks at about 12.2, about 12.9, about 13.3, about 15.6, and about 22.7 degrees 2-theta (±0.15 degrees 2-theta).

In still another embodiment, solid 6-beta-naltrexol hydrochloride may exist as crystalline Form XI$_S$. Crystalline Form XI$_S$ of 6-beta-naltrexol hydrochloride exhibits an X-ray powder diffraction pattern comprising characteristic peaks expressed in degrees 2-theta as diagrammed in FIG. 13. Form XI$_S$ of 6-beta-naltrexol hydrochloride has peaks at 7.971, 10.737, 12.681, 13.478, 15.061, 15.844, 17.294, 18.022, 19.141, 21.541, 22.018, 22.618, 23.002, 24.455, 25.559, 25.861, 26.382, 27.161, 27.336, 28.057, 29.518, 29.799, 31.660, 32.216, 339, 34.143, 34.992, 35.221, 35.842, 37.359, 37.831, 38.302, and 39.219 degrees 2-theta. In particular, Form XI$_S$ has predominant peaks at about 12.7, about 13.5, about 15.1, about 21.5, about 22.0, and about 23.0 degrees 2-theta (±0.15 degrees 2-theta). Form XI$_S$ of 6-beta-naltrexol hydrochloride exhibits a first endotherm from about 25°-125° C. and a second endotherm at about 189°-190° C., as measured by differential scanning calorimetry. Crystalline Form XI$_S$ of 6-beta-naltrexol hydrochloride exhibits a loss of mass of about 0.6-0.7% from about 25°-125° C., as measured by thermogravimetric analysis.

In yet another embodiment, solid 6-beta-naltrexol hydrochloride may exist as an amorphous form. The amorphous form of 6-beta-naltrexol hydrochloride exhibits an X-ray powder diffraction pattern expressed in degrees 2-theta as diagrammed in FIG. 14. Due to the amorphous nature of this form, the X-ray powder diffraction pattern does not reveal any distinct, sharp peaks.

(III) Pharmaceutical Compositions

Another aspect of the invention provides for a pharmaceutical composition comprising at least one polymorphs of 6-beta-naltrexol and at least one pharmaceutically acceptable excipient. In some embodiments, the pharmaceutical composition may comprise at least one crystalline form of the free base of 6-beta-naltrexol and at least one pharmaceutically acceptable excipient, wherein the crystalline form of 6-beta-naltrexol base is selected from the group consisting of Form I$_B$, Form II$_B$, and combinations thereof. Stated another way, the pharmaceutical composition may comprise either of the crystalline forms of 6-beta-naltrexol base or a combination of the two crystalline forms of 6-beta-naltrexol base. The different crystalline forms of 6-beta-naltrexol base are detailed above in section (I).

In other embodiments, the pharmaceutical composition may comprise at least one polymorph of the hydrochloride salt of 6-beta-naltrexol and at least one pharmaceutically acceptable excipient, wherein the polymorph of 6-beta-naltrexol hydrochloride is selected from the group consisting of crystalline Form I$_S$, crystalline Form II$_S$, crystalline Form III$_S$, crystalline Form IV$_S$, crystalline Form V$_S$, crystalline Form VI$_S$, crystalline Form VII$_S$, crystalline Form VIII$_S$, crystalline Form IX$_S$, crystalline Form X$_S$, crystalline Form XI$_S$, an amorphous form, and combinations thereof. Stated another way, the pharmaceutical composition may comprise one, two, three, four, five, six, seven, eight, nine, ten, eleven, or twelve of the different polymorphs of 6-beta-naltrexol hydrochloride. The different polymorphs of 6-beta-naltrexol hydrochloride are detailed above in section (II).

In alternate embodiments, the pharmaceutical composition may comprise at least one polymorph of the free base of 6-beta-naltrexol, at least one polymorph of the hydrochloride salt of 6-beta-naltrexol, and at least one pharmaceutically acceptable excipient.

A variety of excipients commonly used in pharmaceutical formulations may be selected on the basis of several criteria such as, e.g., the desired dosage form and the release profile properties of the dosage form. Non-limiting examples of suitable excipients include an agent selected from the group comprising a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpirrolidone. By way of non-limiting example, the filler may be calcium sulfate, both di-and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), micro-crystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semi-solids; or gels. Other suitable dosage forms include transdermal systems or patches. The transdermal system may be a matrix system, a reservoir system, or a system without rate-controlling membranes.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Golman's The Pharmacological Basis of Therapeutics, Tenth Edition (2001), Appendix II, pp. 475-493, and the Physicians' Desk Reference.

(IV) Processes for Preparing Substantially Pure Polymorphs of 6-Beta-Naltrexol

A further aspect of the present invention provides processes for producing substantially pure polymorphs of 6-beta-naltrexol. The phrase "substantially pure," as used herein, means that the polymorph has a purity of about 95% by weight, or more preferably about 97% by weight, as defined by X-ray powder diffraction. Stated another way, the polymorph has no more than about 5% by weight, or more preferably no more than about 3% by weight, of another polymorph of 6-beta-naltrexol.

In one embodiment, processes are provided for preparing a substantially pure crystalline form of 6-beta-naltrexol base. In another embodiment, processes are provided for preparing a substantially pure crystalline form of 6-beta-naltrexol hydrochloride. In further embodiment, a process is provided for preparing a substantially pure amorphous form of 6-beta-naltrexol hydrochloride. The different polymorphs of 6-beta-naltrexol base and 6-beta-naltrexol hydrochloride are detailed above in sections (I) and (II), respectively.

In general, the process for preparing crystalline forms 6-beta-naltrexol base comprises: a) contacting 6-beta-naltrexol base with a solvent form a saturated or a near saturated solution; and b) forming crystals of the substantially pure crystalline form of 6-beta-naltrexol base. The process for preparing crystalline forms 6-beta-naltrexol hydrochloride comprises: a) contacting 6-beta-naltrexol hydrochloride with a solvent form a saturated or a near saturated solution; and b) forming crystals of the substantially pure crystalline form of 6-beta-naltrexol hydrochloride. The process for preparing the amorphous form of 6-beta-naltrexol hydrochloride comprises: a) contacting 6-beta-naltrexol hydrochloride with a solvent form a saturated or a near saturated solution; and b) evaporating the solvent to form the substantially pure amorphous form of 6-beta-naltrexol hydrochloride.

The solvent used in the process can and will vary depending upon the embodiment. In general, the solvent may be a protic solvent, an aprotic solvent, or combinations thereof. Suitable protic solvents include, but are not limited to, water, methyl alcohol, ethyl alcohol, isopropyl alcohol, n-propyl alcohol, isobutyl alcohol, n-butyl alcohol, s-butyl alcohol, t-butyl alcohol, formic acid, acetic acid, and combinations thereof. Non-limiting examples of suitable aprotic solvents include acetone, acetonitrile, dichloromethane, tetrahydrofuran, and combinations thereof. The free base or the hydrochloride salt of 6-beta-naltrexol that is contacted with the solvent may be in a solid form (e.g., a powder) or a liquid form (e.g., in a solution comprising a co-solvent, or a concentrated oil/gel/gum). The weight ratio of solvent to 6-beta-naltrexol may range from about 2:1 to about 20:1, or more preferably from about 5:1 to about 10:1.

The temperature of the process can and will vary depending upon the embodiment. The temperature of step (a) may range from about 4° C. to about the boiling temperature of the solvent. In one embodiment, step (a) may be conducted at a temperature that ranges from about 4° C. to about 25° C. In another embodiment, step (a) may be conducted at a temperature that ranges from about 25° C. to about 60° C. In still another embodiment, step (a) may be conducted at a temperature that ranges from about 60° C. to about 100° C. In a further embodiment, step (a) may be conducted at a temperature that ranges from about 100° C. to about 150° C. The temperature of step (b) may also range from about −10° C. to about 150° C. In one embodiment, step (b) may be conducted at temperature that ranges from about −10° C. to about 20° C. In another embodiment, step (b) may be conducted at a temperature that ranges from about 20° C. to about 50° C. In an alternate embodiment, step (b) may be conducted at a temperature that ranges from about 50° C. to about 100° C. in another alternate embodiment, step (b) may be conducted at a temperature that ranges from about 100° C. to about 150° C.

The crystals of substantially pure 6-beta-naltrexol may be formed by a variety of methods, as detailed in the Examples. In some embodiments, the crystals may be formed by "slow evaporation." For this, the solvent is typically slowly evaporated such that crystals form slowly. The rate of evaporation may be slowed by placing the saturated or near saturated solution in a flask with a narrow opening, covering the opening with paper or foil comprising a few small holes, or sealing the opening with a cap into which a needle has been inserted. Evaporation of the solvent may be conducted in the presence of air or in an inert environment (i.e., under nitrogen or argon). The solvent may be evaporated at atmospheric pressure or at a pressure that is less than atmospheric pressure. In other embodiments, the crystals may be formed by "hot crystallization" or "hot recrystallization." For this, step (a) of the process is conducted at an elevated temperature. Typically, the temperature of this step is at or near the boiling point of the solvent. The solvent may be removed at an elevated temperature, wherein crystals precipitate out of the hot solution. Alternatively, the hot solution may be allowed to cool, wherein crystals precipitate out of the cool solution.

The process generally further comprises collecting the solids (i.e., crystals or amorphous form) of substantially pure 6-beta-naltrexol. The solids may be collected by filtration, centrifugation, or other techniques well known in the art. The process may further comprise drying the solids of substantially pure 6-beta-naltrexol. The solids may be dried under a vacuum either at room temperature or at an elevated temperature.

In one preferred embodiment, crystalline Form $II_B$ of 6-beta-naltrexol base may be prepared by hot crystallization of 6-beta-naltrexol base in a solvent comprising isopropyl alcohol.

In another preferred embodiment, crystalline Form $I_S$ of 6-beta-naltrexol hydrochloride may be prepared by hot crystallization of 6-beta-naltrexol hydrochloride in water.

In still another preferred embodiment, crystalline Form $II_S$ of 6-beta-naltrexol hydrochloride may be prepared by hot crystallization of 6-beta-naltrexol hydrochloride in a solvent comprising isopropyl alcohol.

In yet preferred embodiment, crystalline Form $III_S$ of 6-beta-naltrexol hydrochloride may be prepared by hot crystallization of 6-beta-naltrexol hydrochloride in water or a mixture of t-butyl alcohol and water.

In another preferred embodiment, crystalline Form $IV_S$ of 6-beta-naltrexol hydrochloride may be prepared by slow evaporation of 6-beta-naltrexol hydrochloride in a solvent comprising ethyl alcohol.

In an alternate preferred embodiment, crystalline Form $V_S$ of 6-beta-naltrexol hydrochloride may be prepared by slow evaporation of 6-beta-naltrexol hydrochloride in a solvent comprising acetonitrile.

In still another preferred embodiment, crystalline Form $VI_S$ of 6-beta-naltrexol hydrochloride may be prepared by either slow evaporation or hot crystallization of 6-beta-naltrexol hydrochloride in a solvent comprising isopropyl alcohol.

In yet another preferred embodiment, crystalline Form $VII_S$ of 6-beta-naltrexol hydrochloride may be prepared by either slow evaporation or hot crystallization of 6-beta-naltrexol hydrochloride in a solvent comprising methyl alcohol.

In a further preferred embodiment, crystalline Form XI$_S$ of 6-beta-naltrexol hydrochloride may be prepared by sublimation of 6-beta-naltrexol hydrochloride.

In yet another preferred embodiment, the amorphous form of 6-beta-naltrexol hydrochloride may be prepared in an alcoholic solvent system.

As various changes could be made in the above compounds and processes without departing from the scope of the invention, it is intended that all matter contained in the above description and in the examples given below, shall be interpreted as illustrative and not in a limiting sense.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

General Protocols

Slow Evaporation. To form crystals by slow evaporation, a saturated or near saturated solution was prepared by mixing 6-beta-naltrexol base or 6-beta-naltrexol hydrochloride in the appropriate solvent or solvent system. A small vial of the saturated/near saturated solution was placed in a nitrogen-purged desiccator at room temperature. Following crystal growth, the crystals were filtered from the residual solvent, if necessary, using a fritted disc funnel.

Hot Crystallization. To form crystals by hot crystallization, the appropriate solvent was heated to boiling or near boiling, and 6-beta-naltrexol base or 6-beta-naltrexol hydrochloride was slowly added until the solution was saturated or near saturated. The solution was allowed to cool at room temperature. Following crystal growth, the crystals typically were filtered from the solvent using a fritted disc funnel. In some experiments, the filtrates were then allowed to slowly evaporate under nitrogen purge to encourage crystal growth. In some cases, the crystals were dried at elevated temperatures.

Slurry Experiments. The stability of the crystalline forms was analyzed using slurry experiments. A portion of the solvent of interest was saturated with 6-beta-naltrexol base or 6-beta-naltrexol hydrochloride in a small vial. Additional 6-beta-naltrexol base or 6-beta-naltrexol hydrochloride was then added to the vial, and the resulting slurry was stirred using a magnetic stir bar.

X-Ray Powder Diffraction. The powder X-ray diffraction pattern (pXRD) was determined using a Siemens D500 X-ray diffractometer (Siemens Diagnostics, Deerfield, Ill.). The instrument was equipped with a long fine focus X-ray tube (with a copper Kα radiation source operated at 40 kV/30 mA), and a diffracted beam monochromator mounted in front of a scintillation detector. The instrument parameters included a scan range of 2.0 to 40.0 degrees 2-theta, a step size of 0.02 degree 2-theta, and a scan time of 1.0 second per step. The instrument was interfaced with a computer for data acquisition and analysis using Materials Data, Inc. software including DataScan and Jade. Each sample was uniformly crushed with a spatula edge and placed on a quartz, zero-background holder.

Differential Scanning Calorimetry. Differential scanning calorimetry (DCS) was performed using a Q100 modulated differential scanning calorimeter (TA Instruments; New Castle, Del.); the instrument was calibrated using Indium. Each sample was weighed into a hermetic aluminum sample pan and sealed with a pinhole lid. The samples were heated from 25° C. to the designated temperature at a rate of 5° C. per minute, unless otherwise indicated.

Thermogravimetric Analysis. Thermogravimetric analysis (TGA) was performed with a Q50 thermogravimetric analyzer (TA Instruments) (equipped with a quartz lined evolved gas furnace for TGA-Fourier transform infrared (FTIR) experiments). The FTIR spectrometer for the TGA-FTIR analyses was a Nicolet Nexus 470 (Thermo Fisher Scientific) equipped with a TGA interface furnace, gas cell and a transfer line. Analyses were performed using OMNIS/Series software. Each sample was weighed into an aluminum sample pan and placed into the instrument. The samples were heated from room temperature to the designated temperature at a rate of 10° C. per minute, unless otherwise indicated, with a nitrogen flow of 50 mL per minute. For the TGA-FTIR experiments, the transfer line and TGA interface furnace were held at 150° C. A Gram-Schmidt plot/analysis was attained for each experiment, with individual spectra of evolved gases analyzed as follows: 16 scans, 8 cm$^{-1}$. A background (16 scans) was acquired prior to each experiment.

Single Crystal X-Ray Diffraction. Single crystal X-ray structures were collected at the University of Missouri-St. Louis Center for Nano Science. X-ray powder diffraction patterns were simulated from the single crystal structures and compared to experimental patterns using the Materials Data, Inc. software package Jade.

Water Vapor Sorption. Data were collected with a SGA-100 water vapor sorption balance (VTI Corporation, Hialeah, Fla.). A portion of the selected sample was weighed into a platinum sample pan and placed into the instrument. The sample was cycled from low (5%) relative humidity (RH) to high (95%) RH to low humidity (i.e., sorption and desorption events) at a constant temperature of 25° C., in 5% RH intervals. The sample was held at each interval until the equilibrium condition was met (i.e., 0.0005% for 3 min, with a maximum of 600 min).

Example 1

Preparation and Characterization of Form I$_B$ Crystals

Form I$_B$ of 6-beta-naltrexol base is a monohydrate, having from about 4.5-5.3% by weight of water. Form I$_B$ crystals were prepared by slow evaporation by mixing 6-beta-naltrexol base with one the following solvents: 1) acetone; 2) methyl alcohol:water (3:1); 3) methyl alcohol; 4) ethyl alcohol:water (7:3); 5) ethyl alcohol; or 6) isopropyl alcohol:water (3:1). Form I$_B$ crystals were also prepared by hot crystallization by mixing 6-beta-naltrexol base with 1) ethyl alcohol or 2) t-butyl alcohol:water (95:5). The stability of the crystals was tested in 1) an isopropyl alcohol slurry; 2) an ethyl alcohol slurry; and 3) a water slurry.

FIG. 1 presents the characteristic X-ray powder diffraction pattern for Form I$_B$. Form I$_B$ exhibited diffraction peaks above background at 6.240, 8.838, 9.820, 10.920, 11.780, 14.001, 15.941, 17.200, 17.680, 18.240, 18.818, 19.781, 20.460, 21.021, 21.259, 22.379, 23.839, 24.299, 24.759, 25.721, 26.781, 27.760, 28.360, 28.935, 29.941, 30.639, 31.541, 32.341, 33.082, 33.718, 35.540, 36.298, 37.518, and 38.139 degree 2-theta. This crystalline form had predominant peaks at about 9.8, about 14.0, about 15.9, about 17.2, about 17.7, and about 22.4 degrees 2-theta (±0.15 degrees 2-theta).

DSC traces of Form $I_B$ showed an endotherm/exotherm at about 75°-125° C., and an endotherm at about 185°-190° C. TGA traces exhibited a loss of mass of 4.0-6.0% at when heated from about 75° to about 160° C. The loss of mass was identified as water.

Example 2

Preparation and Characterization of Form $II_B$ Crystals

Form $II_B$ of 6-beta-naltrexol base is an anhydrous form. It was prepared by hot recrystallization of Form $I_B$ in a mixture of isopropyl alcohol and water.

Figure 2:
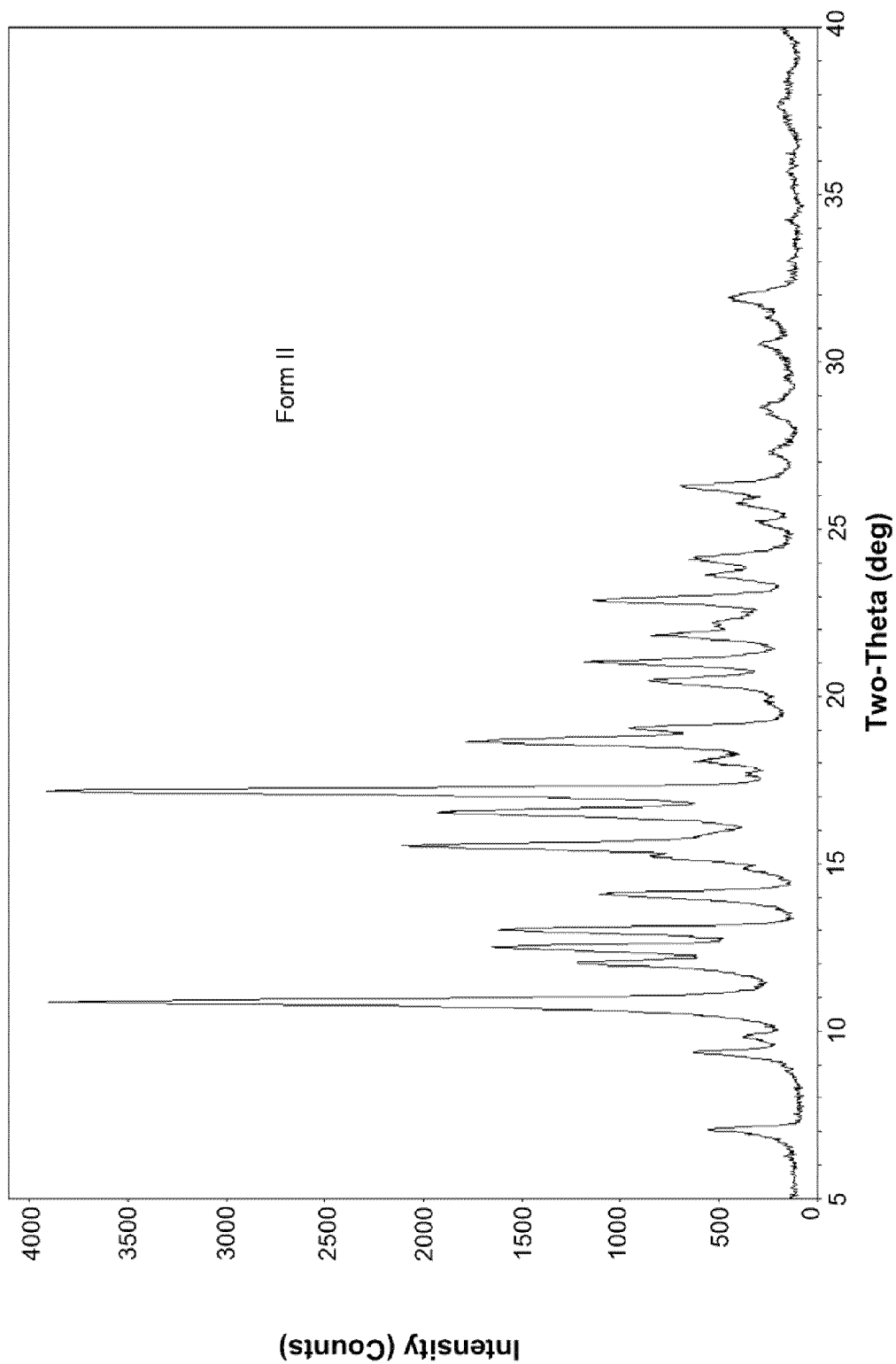
FIG. 2 represents an X-ray powder diffraction pattern of crystalline Form II of 6-beta-naltrexol base. Peak intensity is plotted as a function of degrees 2-theta.

FIG. 2 presents the characteristic X-ray powder diffraction pattern for Form $II_B$. The diffraction pattern displayed peaks above background at 7.098, 9.381, 9.859, 10.900, 12.060, 12.539, 13.041, 14.120, 14.842, 15.221, 15.560, 16.542, 17.182, 18.081, 18.661, 19.061, 20.499, 21.042, 21.843, 22.219, 22.900, 23.660, 24.121, 25.200, 25.800, 26.300, 27.359, 28.642, 30.558, 31.359, 31.920, 34.257, 35.704, and 37.678 degrees 2-theta. Form $II_B$ exhibited predominant peaks at about 10.9, about 15.6, about 16.5, about 17.2, and about 18.7 (±0.15 degrees 2-theta).

DSC traces of Form $II_B$ showed an endotherm/exotherm from 90-110° C., and an endotherm at approximately 189-190° C. TGA scans of Form $II_B$ showed a loss of mass of 0.2-0.3% over a temperature range of 75-125° C.

Form $II_B$ exhibited a greater solubility in a mixture of alcohol and water than Form $I_B$, and Form $II_B$ appeared to be more resistant to degradation in air than Form $I_B$.

Example 3

Preparation and Characterization of Form $I_S$ Crystals

Form $I_S$ of 6-beta-naltrexol hydrochloride salt is an anhydrous form. Form $I_S$ crystals were prepared by hot recrystallization by dissolving 6-beta-naltrexol HCl salt of other forms (primarily solvates) in water. The solvent was then removed at an elevated temperature to give solid Form $I_S$.

Figure 3:
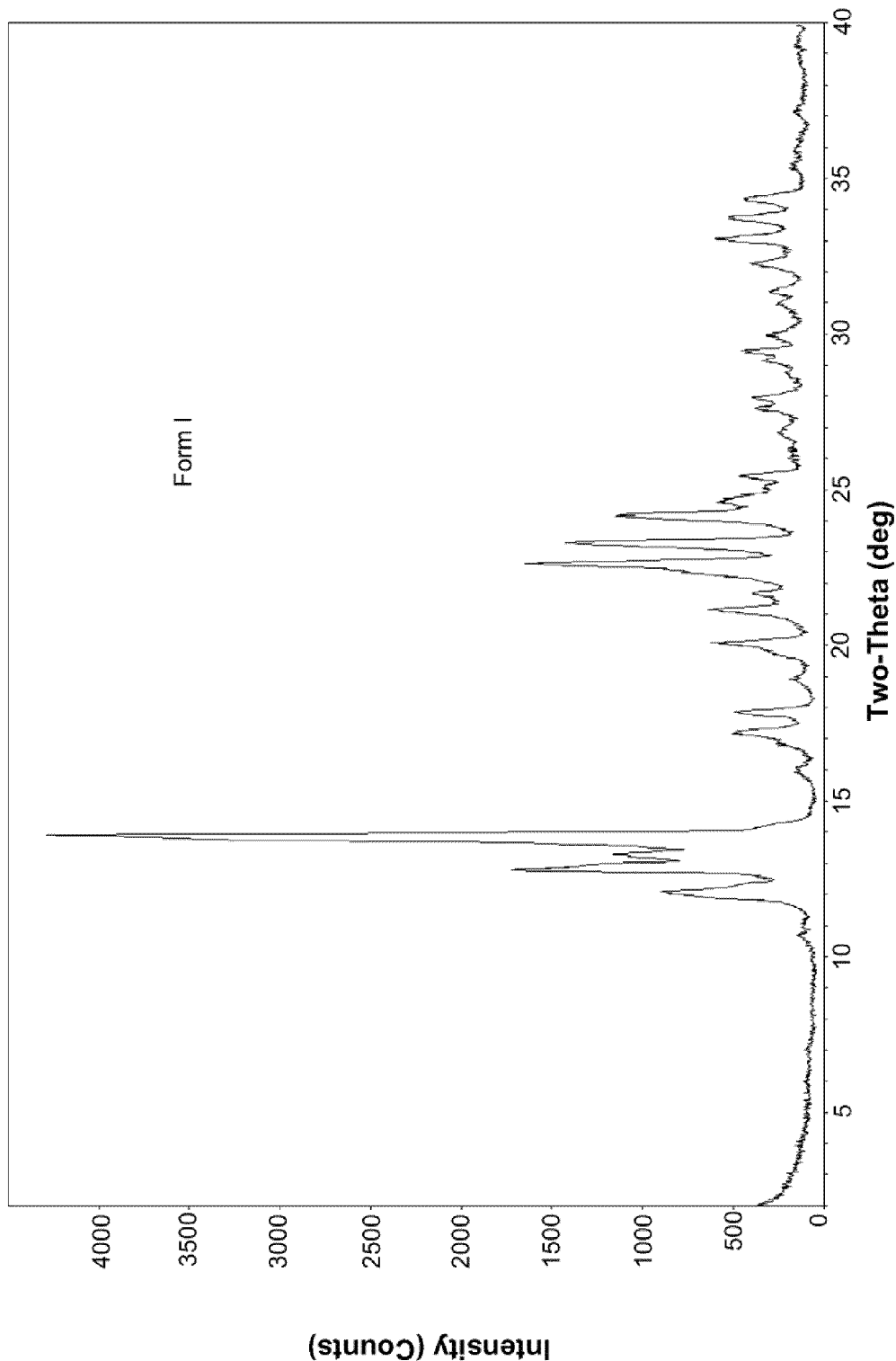
FIG. 3 represents an X-ray powder diffraction pattern of crystalline Form I of 6-beta-naltrexol hydrochloride. Peak intensity is plotted as a function of degrees 2-theta.

The X-ray powder diffraction pattern of Form $I_S$ is presented in FIG. 3. The pattern comprised peaks above background at 10.739, 12.101, 12.821, 13.321, 13.939, 15.943, 16.860, 17.182, 17.880, 18.938, 19.822, 20.101, 21.181, 21.682, 22.659, 23.339, 24.180, 24.680, 25.464, 26.843, 27.656, 27.997, 29.162, 29.498, 30.015, 30.982, 31.399, 32.301, 33.081, 33.798, 34.340, 35.441, 35.920, 37.216, and 39.320 degrees 2-theta. Form $I_S$ exhibited predominant peaks at about 12.8, about 13.9, about 22.7, about 23.3, and about 24.2 degrees 2-theta (±0.15 degrees 2-theta).

Form $I_S$ exhibited a DSC trace with a small, broad endotherm from 40°-100° C., and an exotherm/endotherm above 190° C. The TGA trace of Form $I_S$ showed a loss of mass of 0.2-0.3% when heated from 40°-100° C.

Example 4

Preparation and Characterization of Form $II_S$ Crystals

Form $II_S$ of 6-beta-naltrexol hydrochloride salt is an isopropyl alcohol solvate. Form $II_S$ crystals were made by dissolving 6-beta-naltrexol base in hot isopropyl alcohol, followed by the addition of aqueous hydrochloric acid. The isopropyl alcohol solvate precipitated from the solution upon cooling. The stability of Form $II_S$ was examined using an isopropyl alcohol slurry experiment; the form was stable for at least 8 days.

Figure 4:
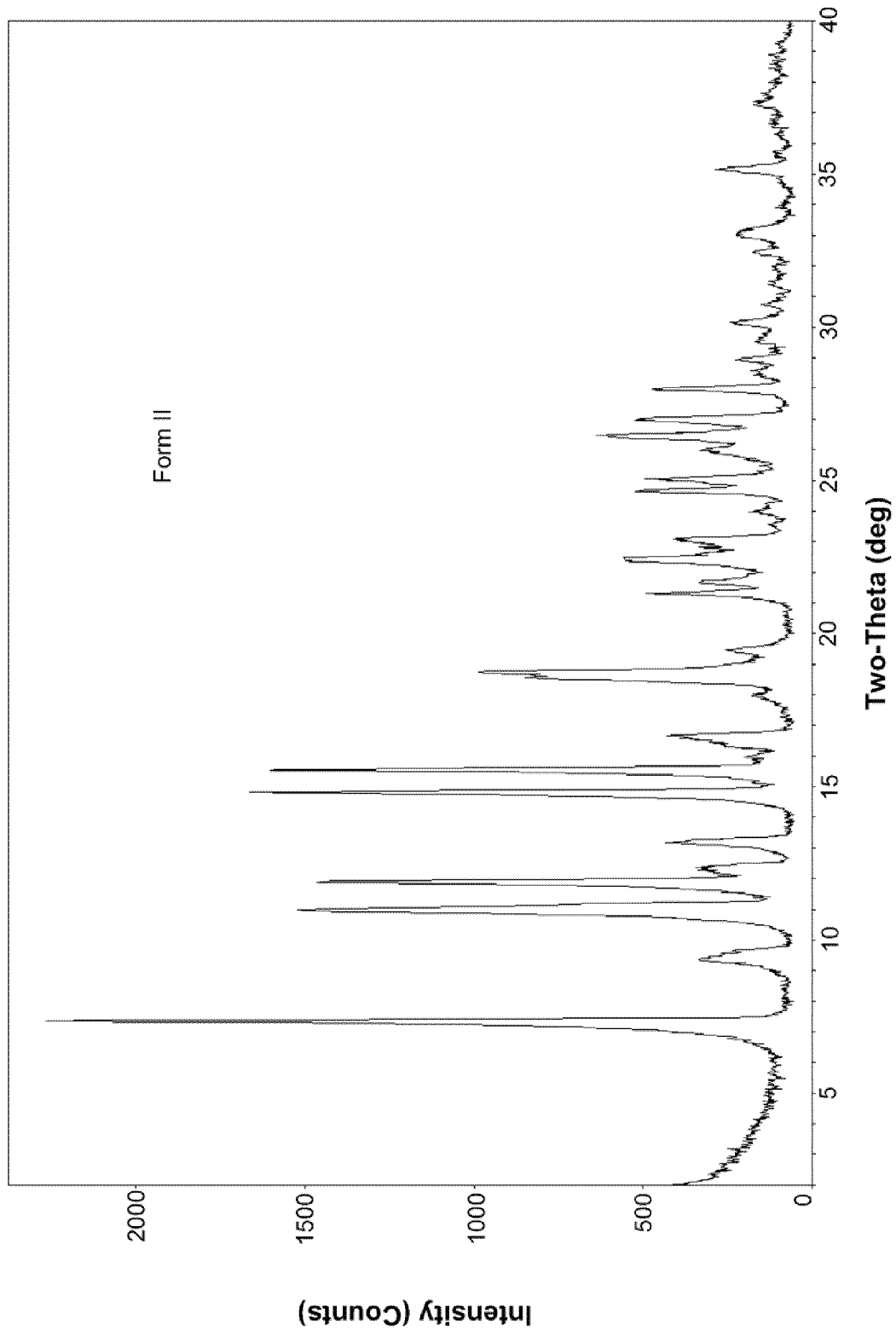
FIG. 4 represents an X-ray powder diffraction pattern of crystalline Form II of 6-beta-naltrexol hydrochloride. Peak intensity is plotted as a function of degrees 2-theta.

FIG. 4 presents the X-ray powder diffraction pattern of Form $II_S$. Form $II_S$ exhibited diffraction peaks above background at 7.398, 9.399, 11.019, 11.922, 12.378, 13.219, 14.859, 15.582, 16.003, 16.462, 16.700, 18.002, 18.761, 19.499, 21.340, 21.720, 22.498, 23.120, 24.001, 24.682, 25.080, 26.003, 26.499, 27.002, 28.002, 28.481, 28.962, 29.579, 30.197, 30.761, 31.419, 31.983, 32.462, 33.021, 35.181, 35.750, 36.678, 37.282, and 38.909 degrees 2-theta. Form $II_S$ had predominant peaks at about 7.4, about 11.0, about 11.9, about 14.9, about 15.6, and about 18.8 degrees 2-theta (±0.15 degrees 2-theta).

Example 5

Preparation and Characterization of Form $III_S$ Crystals

Form $III_S$ of 6-beta-naltrexol hydrochloride can exist in either an anhydrous or a hydrated form. The fully hydrated state of this form is a dihydrate, with approximately 8.5% water. Form $III_S$ crystals were prepared by dissolving a 6-beta-naltrexol hydrochloride alcoholic solvate in a small amount of hot water. The solvent was subsequently removed at an elevated temperature, and the crystals precipitated from the hot solution. Form $III_S$ crystals were also prepared by dissolving 6-beta-naltrexol base in a hot mixture of t-butyl alcohol and water (95:5), and then adding concentrated hydrochloric acid. Upon cooling, crystals precipitated from the solution.

Figure 5:
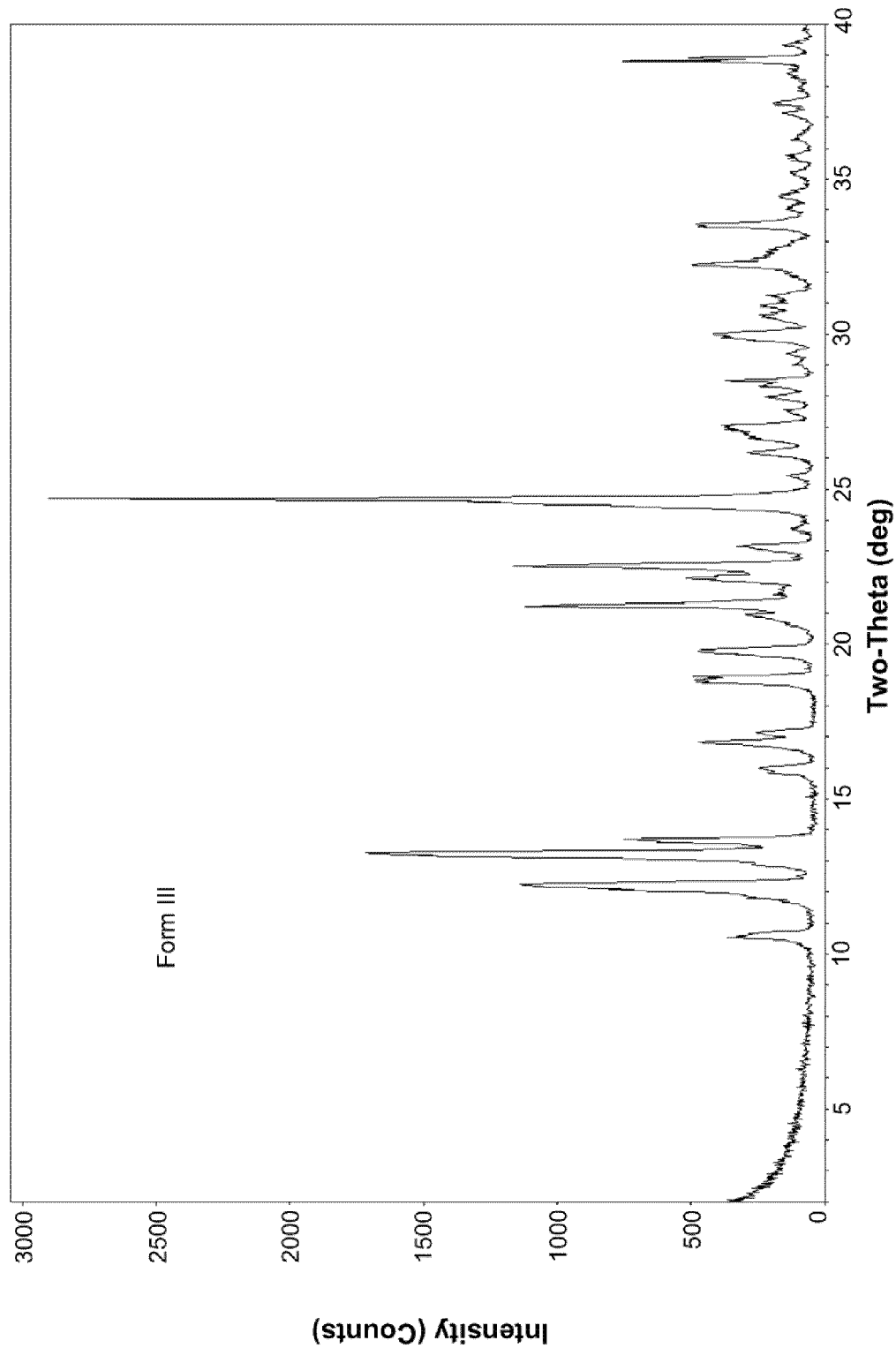
FIG. 5 represents an X-ray powder diffraction pattern of crystalline Form III of 6-beta-naltrexol hydrochloride. Peak intensity is plotted as a function of degrees 2-theta.

FIG. 5 presents the characteristic pXRD pattern of Form $III_S$. The pXRD scan displayed peaks above background at 10.581, 12.279, 13.300, 13.721, 16.022, 16.861, 17.180, 18.899, 19.800, 20.962, 21.261, 22.160, 22.542, 23.200, 23.792, 24.718, 25.477, 26.202, 26.781, 27.095, 27.577, 28.021, 28.362, 28.537, 29.046, 29.402, 30.020, 30.637, 30.924, 31.281, 32.279, 32.698, 33.577, 34.120, 34.498, 35.253, 35.702, 36.359, 37.144, 37.462, 37.901, 38.458, 38.844, and 39.377 degrees 2-theta. Form $III_S$ had predominant peaks at about 12.3, about 13.3, about 21.3, about 22.5, about 24.7, and about 38.8 degrees 2-theta (±0.15 degrees 2-theta).

DSC traces of Form $III_S$ exhibited a broad endotherm from 25°-125° C., and an endotherm above 175° C. TGA traces of Form $III_S$ showed a loss of mass of 7.0-9.0% when heated from 25°-125° C. FTIR identified the loss of mass as water.

Water vapor sorption analysis revealed that Form $III_S$ lost approximately 4.5% of its original 8.9% water content upon subjection to humidities below 15% RH. Above 15% RH, Form $III_S$ appeared to be reasonably stable up to approximately 90% RH. Above this humidity, Form $III_S$ absorbed approximately 1.4%-1.5% water at 95% RH. During desorption, Form $III_S$ showed similar behavior (minimal hysteresis was observed). Upon the conclusion of this experiment, the sample still comprised predominately Form $III_S$, as determined by pXRD analysis. The dihydrate form of Form $III_S$ appears to be the most stable of all the crystalline forms of 6-beta-naltrexol hydrochloride.

Example 6

Preparation and Characterization of Form $IV_S$ Crystals

Form $IV_S$ of 6-beta-naltrexol hydrochloride is an ethyl alcohol solvate. Form $IV_S$ crystals were prepared by reacting 6-beta-naltrexol base with hydrochloric acid in an ethyl alcohol solution, and slow evaporation of the solvent. The ethyl alcohol solutions included 1) ethyl alcohol; 2) acetone and ethyl alcohol (2:1.3); and 3) isopropyl alcohol and ethyl alcohol (8:5). Form $IV_S$ crystals were also prepared by hot recrystallization of other forms of 6-beta-naltrexol hydrochloride in ethyl alcohol. The stability of Form $IV_S$ crystals was examined in ethyl alcohol slurry experiments. The form was stable for at least 15 days.

Figure 6:
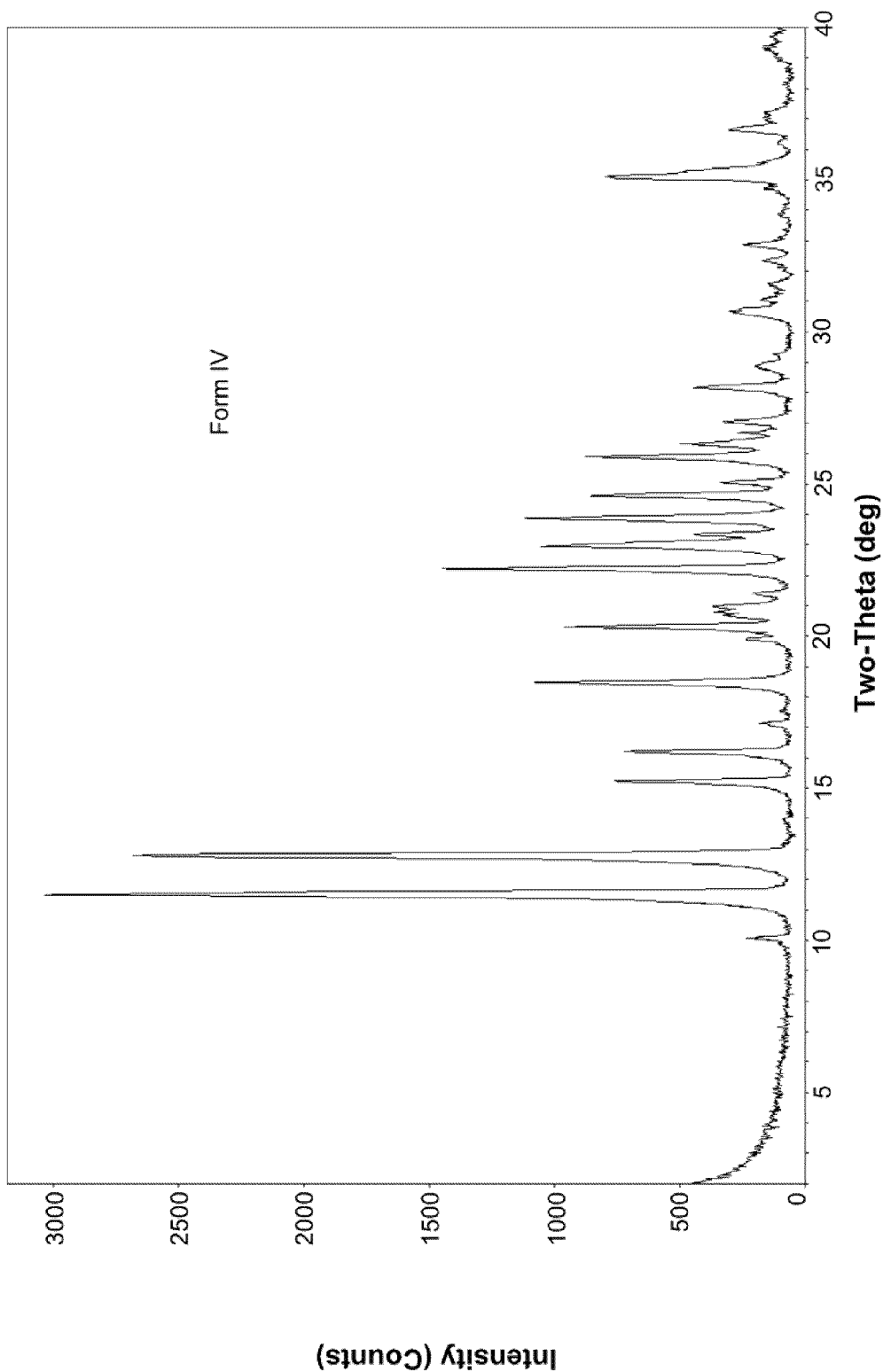
FIG. 6 represents an X-ray powder diffraction pattern of crystalline Form IV of 6-beta-naltrexol hydrochloride. Peak intensity is plotted as a function of degrees 2-theta.

FIG. 6 presents the characteristic pXRD pattern of Form $IV_S$. The scan revealed peaks above background at 10.118, 11.523, 12.820, 14.017, 15.275, 16.240, 17.160, 18.518, 19.924, 20.341, 20.823, 21.001, 21.452, 22.258, 22.982, 23.380, 23.918, 24.643, 25.080, 25.921, 26.340, 26.720, 27.079, 28.201, 28.919, 29.297, 30.718, 31.082, 31.624, 32.381, 32.899, 33.899, 34.774, 35.120, 36.258, 36.663, 37.239, 39.084, and 39.354 degrees 2-theta. Form $IV_S$ had predominant peaks at about 11.5, about 12.8, about 18.5, about 22.3, about 23.0, and about 23.9 degrees 2-theta (±0.15 degrees 2-theta).

DSC traces of Form $IV_S$ showed an endotherm from 150°-200° C. At times, these traces also showed a broad endotherm from 25°-125° C. TGA traces for Form $IV_S$ showed a loss of mass of 6.0-12.0% in the temperature range of 150°-200° C. FTIR identified the loss of mass as ethyl alcohol. The samples that exhibited the broad endotherm from 25°-125° C. also showed a loss of mass of 0.5-3% when heated over this temperature range. The loss of mass was identified as water.

Example 7

Preparation and Characterization of Form $V_S$ Crystals

Form $V_S$ of 6-beta-naltrexol hydrochloride is an acetonitrile solvate. Form $V_S$ crystals were prepared by slow evaporation of 6-beta-naltrexol hydrochloride in a mixture of acetonitrile and methyl alcohol (2:1). Form $V_S$ was also prepared by reacting 6-beta-naltrexol base with hydrochloric acid in an acetonitrile solution.

Figure 7:
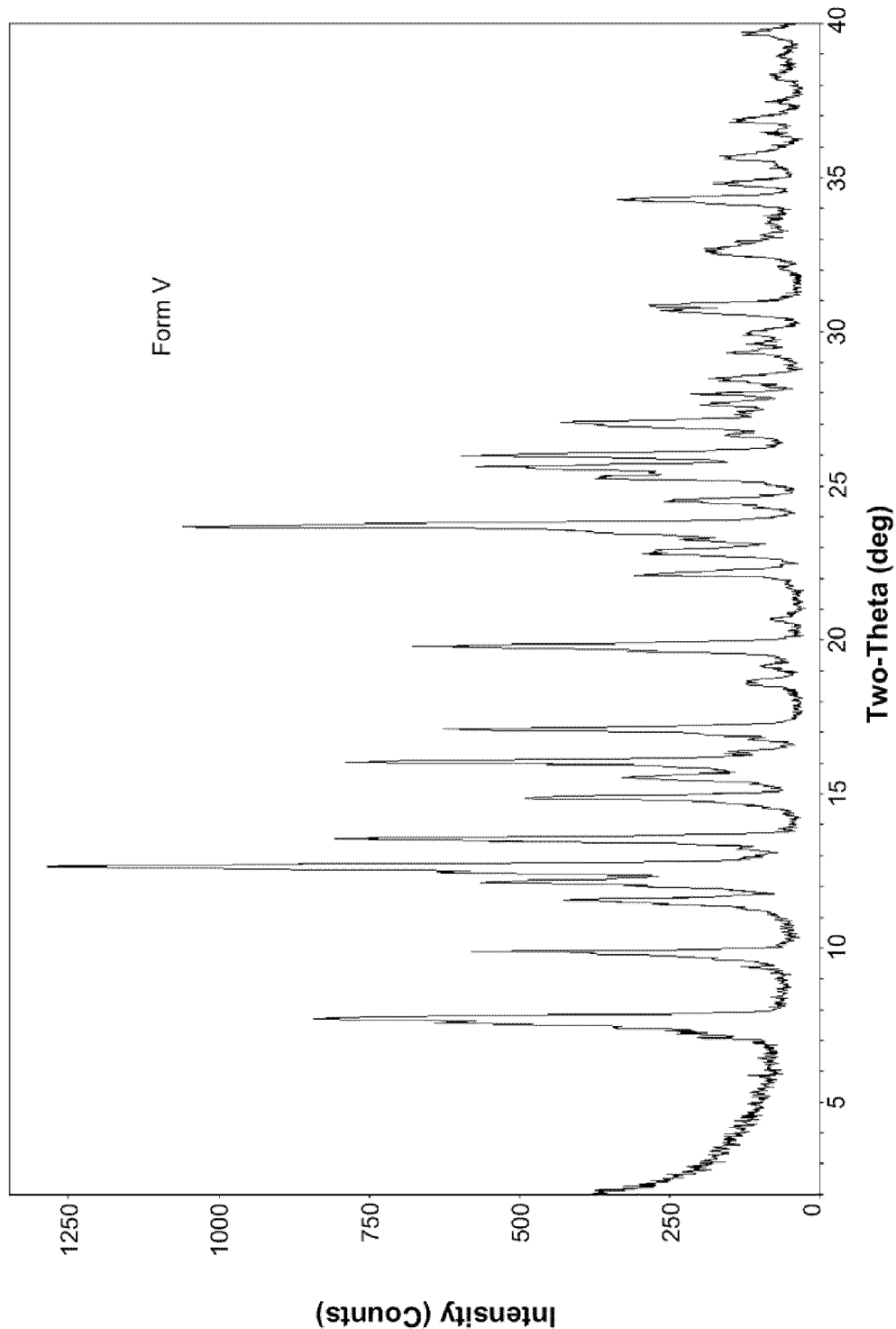
FIG. 7 represents an X-ray powder diffraction pattern of crystalline Form V of 6-beta-naltrexol hydrochloride. Peak intensity is plotted as a function of degrees 2-theta.

The pXRD pattern of Form $V_S$ is presented in FIG. 7. The pattern comprises peaks above background at 7.261, 7.759, 9.420, 9.938, 11.600, 12.163, 12.681, 13.583, 14.903, 15.580, 16.065, 16.399, 17.138, 18.599, 19.198, 19.822, 20.686, 22.143, 22.822, 23.299, 23.702, 24.544, 25.282, 25.660, 26.020, 26.679, 27.098, 27.664, 28.000, 28.519, 29.359, 29.626, 30.000, 30.897, 32.641, 34.320, 34.896, 35.718, 36.497, 36.844, 37.498, 38.360, and 38.959 degrees 2-theta. Form $V_S$ exhibited predominant peaks at about 7.8, about 12.7, about 13.6, about 16.1, about 19.8, and about 23.7 degrees 2-theta (±0.15 degrees 2-theta).

DSC traces of Form $V_S$ exhibited an endotherm from 1.0-150° C., and a broad endotherm/exotherm from 175°-200° C. TGA traces of Form $V_S$ showed a loss of mass of 1.0-1.5% from 75°-125° C. and another loss of mass of 8.0-9.0% from 150°-180° C. FTIR identified both losses of mass as predominately acetonitrile.

Example 8

Preparation and Characterization of Form $VI_S$ Crystals

Form $VI_S$ of 6-beta-naltrexol hydrochloride is an isopropyl alcohol solvate. Form $VI_S$ was prepared by reacting 6-beta-naltrexol base with hydrochloric acid in a solution of isopropyl alcohol, and forming crystals by slow evaporation. Form $VI_S$ crystals were also prepared by hot recrystallization of 6-beta-naltrexol hydrochloride in isopropyl alcohol.

Figure 8:
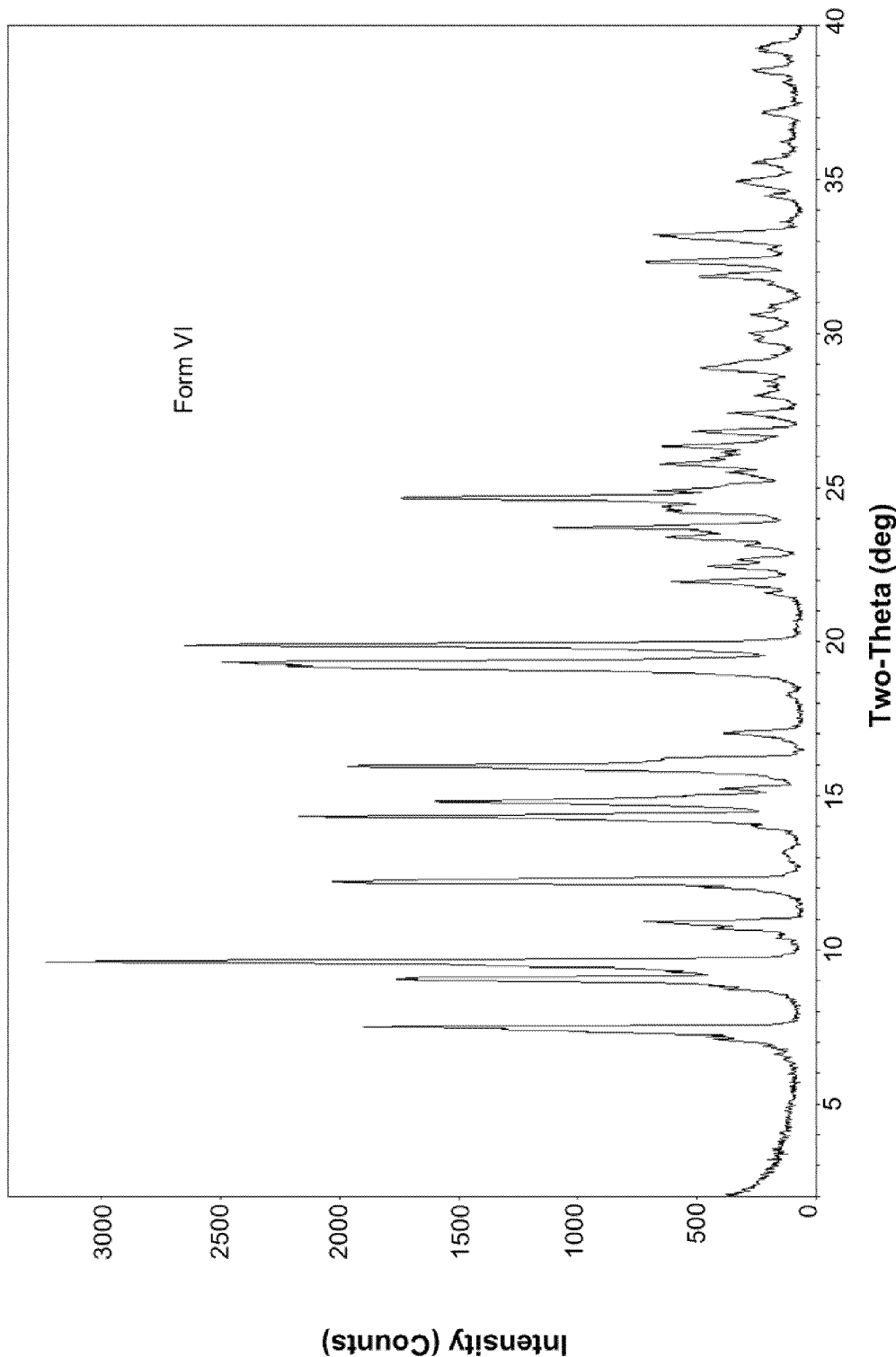
FIG. 8 represents an X-ray powder diffraction pattern of crystalline Form VI of 6-beta-naltrexol hydrochloride. Peak intensity is plotted as a function of degrees 2-theta.

FIG. 8 presents the characteristic pXRD pattern of Form $VI_S$. The form exhibited peaks above background at 7.138, 7.538, 9.082, 9.658, 10.939, 12.240, 13.181, 14.361, 14.858, 15.262, 15.983, 16.239, 17.097, 18.301, 19.359, 19.921, 21.619, 21.980, 22.481, 22.699, 23.161, 23.439, 23.740, 24.340, 24.701, 24.955, 25.541, 25.800, 26.363, 26.859, 27.459, 28.020, 28.498, 28.938, 29.819, 30.040, 30.640, 30.885, 31.899, 32.342, 33.220, 34.501, 34.960, 35.566, 36.259, 37.181, 38.190, 38.579, and 39.281 degrees 2-theta. Form $VI_S$ had predominant peaks at about 9.7, about 12.2, about 14.4, about 16.0, about 19.4, and about 19.9 degrees 2-theta (±0.15 degrees 2-theta).

DSC traces of Form $VI_S$ exhibited a broad endotherm from 150°-180° C. followed by an exothermic transition. TGA traces of Form $VI_S$ showed a loss of mass of 7.0-8.0% from 150°-200° C., and a loss of mass of 1.0-2.0% from 200°-225° C. These were identified as being associated with the loss of isopropyl alcohol.

Example 9

Preparation and Characterization of Form $VII_S$ Crystals

Form $VII_S$ of 6-beta-naltrexol hydrochloride is a methyl alcohol solvate. Form $VII_S$ was prepared by reacting 6-beta-naltrexol base with hydrochloric acid in a solution of methyl alcohol, and forming crystals by slow evaporation. Form $VII_S$ crystals were also prepared by hot recrystallization of 6-beta-naltrexol hydrochloride in methyl alcohol.

Figure 9:
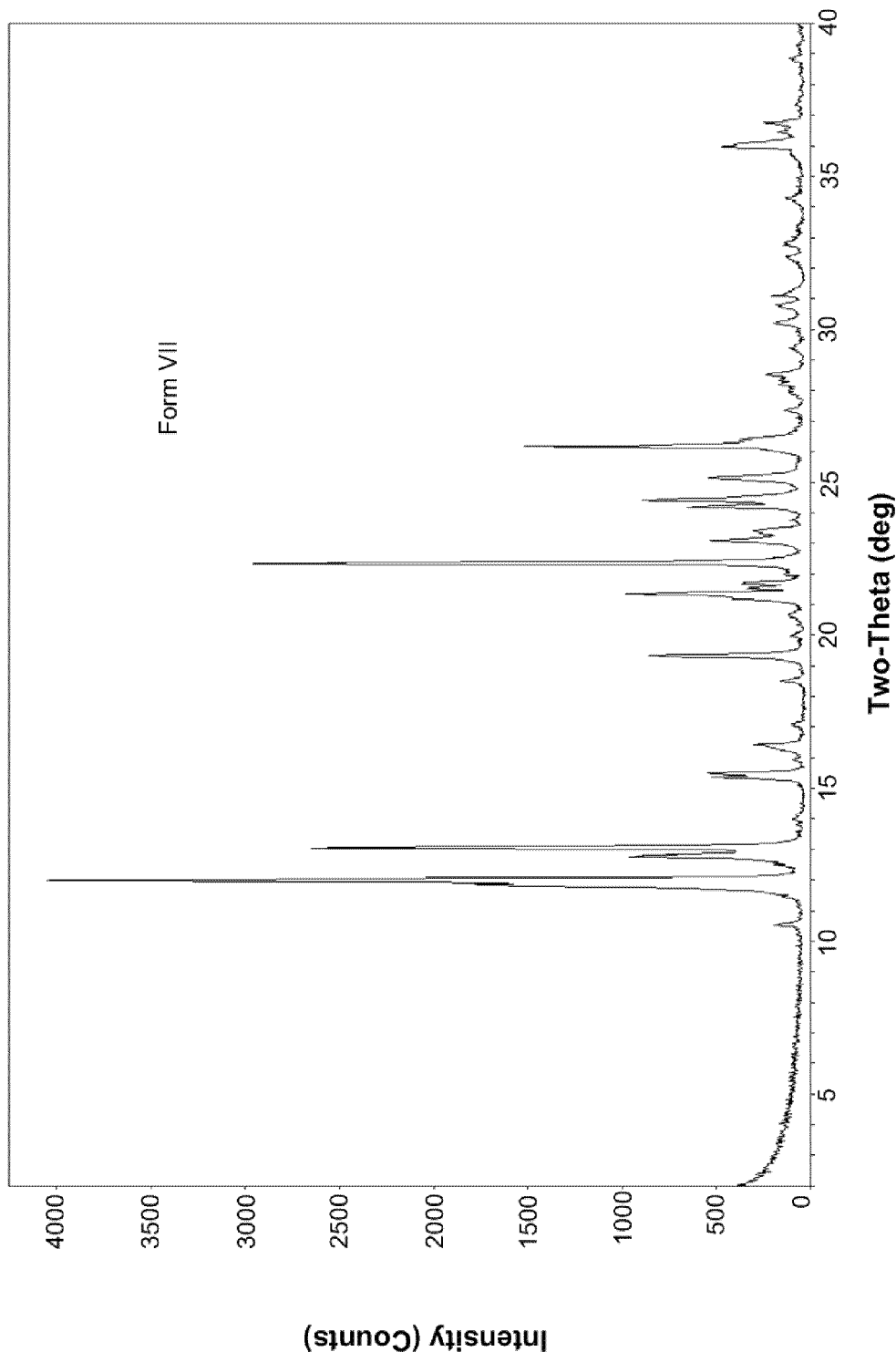
FIG. 9 represents an X-ray powder diffraction pattern of crystalline Form VII of 6-beta-naltrexol hydrochloride. Peak intensity is plotted as a function of degrees 2-theta.

The pXRD pattern of Form $VII_S$ is presented in FIG. 9. Form $VII_S$ exhibited peaks above background at 10.580, 12.021, 12.803, 13.084, 14.040, 15.520, 15.947, 16.457, 17.102, 18.538, 19.376, 20.021, 20.683, 21.383, 21.727, 22.369, 23.138, 23.459, 24.224, 24.443, 25.162, 26.202, 26.457, 27.383, 28.041, 28.224, 28.544, 29.418, 30.225, 30.820, 31.128, 32.410, 32.781, 34.335, 35.987, 36.479, 36.774, 37.371, 38.903, and 39.300 degrees 2-theta. The form had predominant peaks at about 12.0, about 13.1, about 21.4, about 22.4, and about 26.2 degrees 2-theta (±0.15 degrees 2-theta).

DSC traces of Form $VII_S$ showed broad endotherms from 50°-125° C. and 170°-200° C. TGA traces of Form $VII_S$ exhibited a loss of mass of 0.4-0.6% from 75°-125° C. and a loss of mass of 7.0-8.0% from 150°-200° C. These were identified as being associated with the loss of methyl alcohol.

Example 10

Characterization of Form $VIII_S$ Crystals

Figure 10:
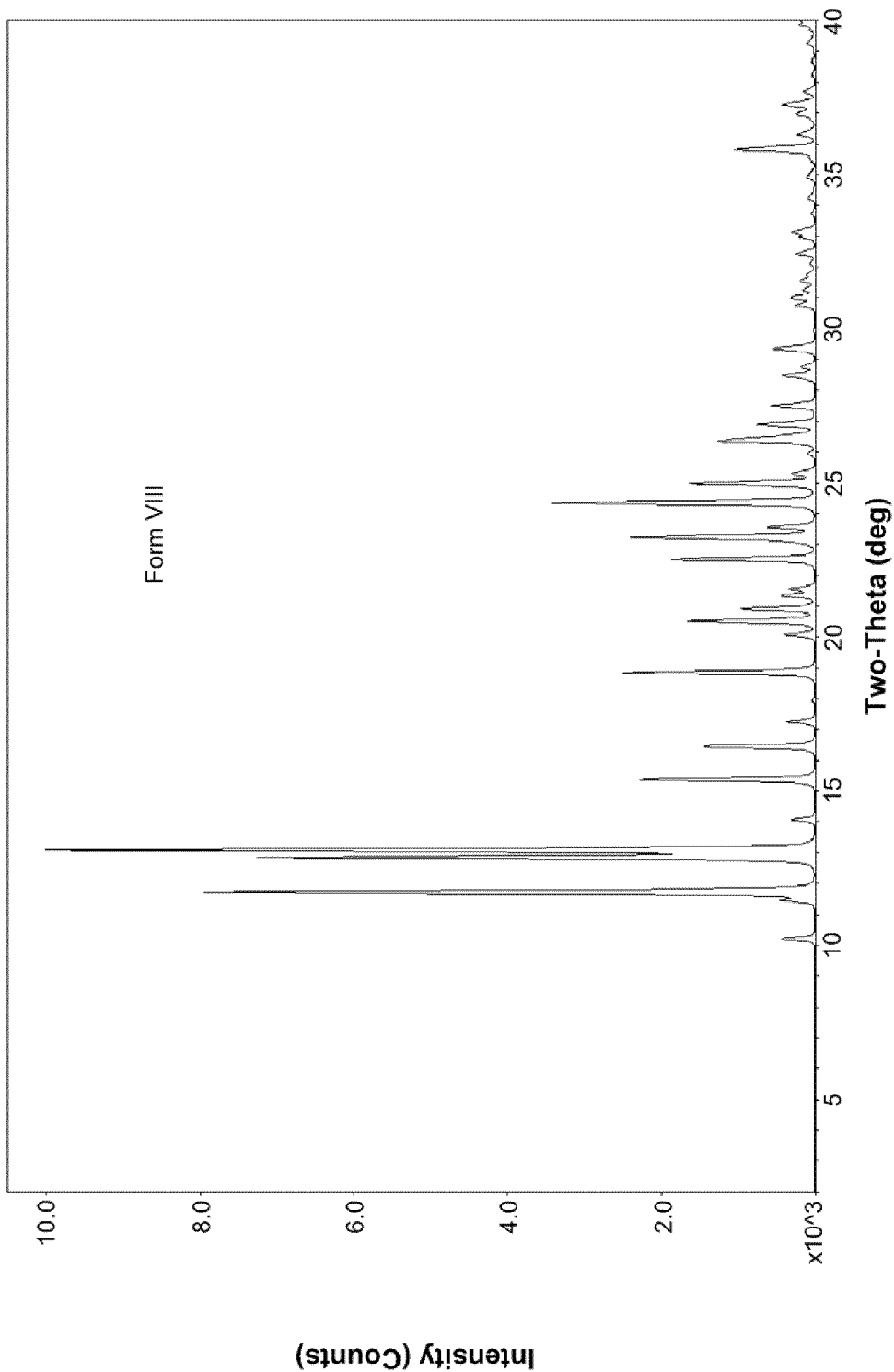
FIG. 10 represents an X-ray powder diffraction pattern simulated from single crystal X-ray diffraction data gathered from the analysis of crystalline Form VIII of 6-beta-naltrexol hydrochloride. Peak intensity is plotted as a function of degrees 2-theta.

Form $VIII_S$ of 6-beta-naltrexol hydrochloride is an ethyl alcohol solvate. The structure of Form $VIII_S$ was solved by SCXRD and FIG. 10 presents the simulated pXRD pattern of this form. Form $VIII_S$ displayed diffraction peaks above background at 10.221, 11.480, 11.740, 12.862, 13.099, 14.097, 15.383, 16.461, 17.262, 17.958, 18.860, 20.082, 20.522, 20.920, 21.359, 21.562, 22.523, 23.258, 23.663, 24.361, 24.982, 25.319, 25.959, 26.362, 26.902, 27.502, 28.500, 28.763, 29.361, 30.761, 31.002, 31.262, 31.544, 31.759, 32.102, 32.440, 33.140, 33.723, 34.240, 34.921, 35.820, 36.283, 36.962, 37.262, 37.681, 38.222, 38.643, 39.243, and 39.880 degrees 2-theta. This from exhibited predominant peaks at about 11.7, about 12.9, about 13.1, about 18.9, and about 24.4 degrees 2-theta (±0.15 degrees 2-theta).

Example 11

Characterization of Form IX$_S$ Crystals

Figure 11:
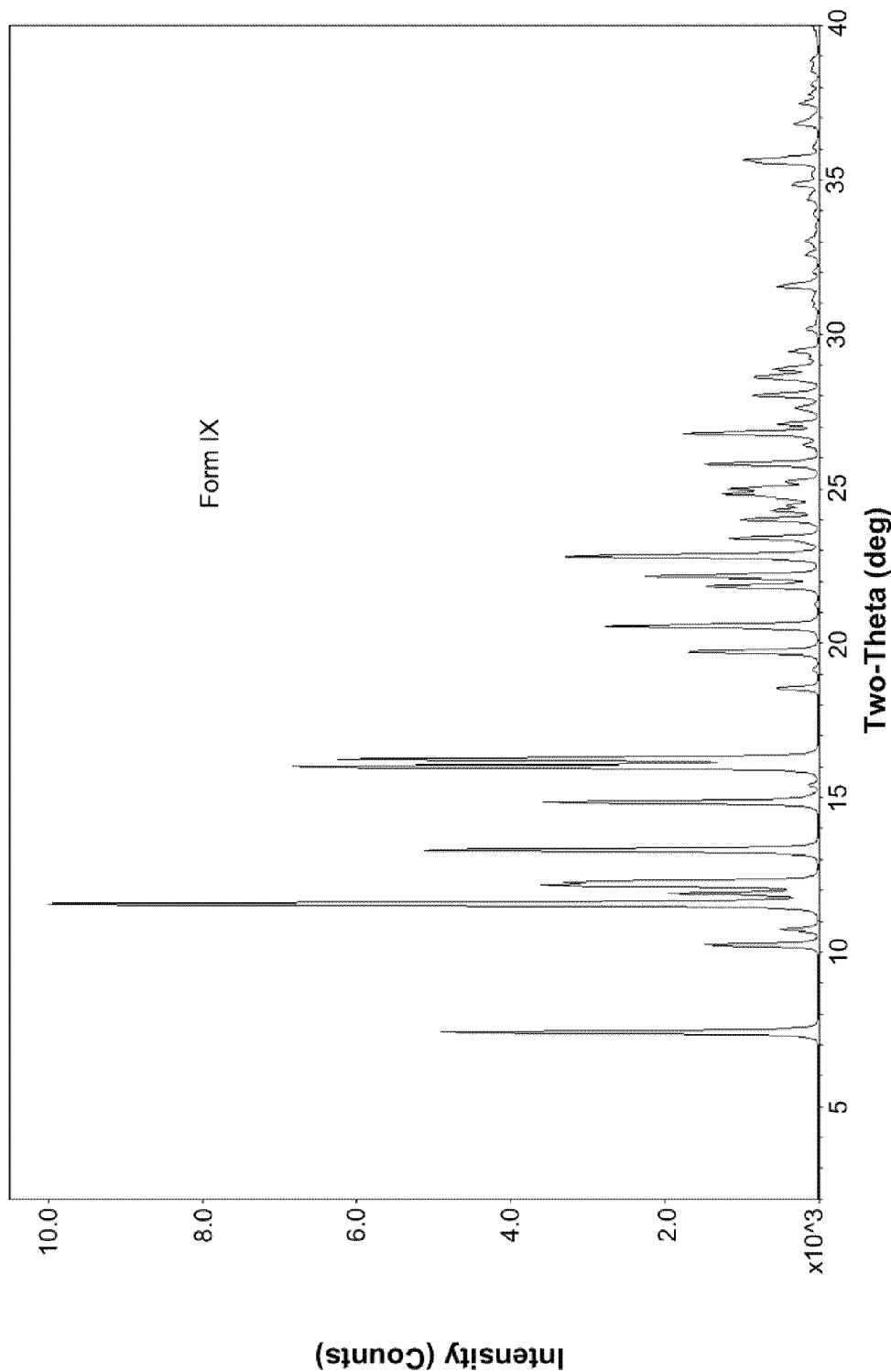
FIG. 11 represents an X-ray powder diffraction pattern simulated from single crystal X-ray diffraction data gathered from the analysis of crystalline Form IX of 6-beta-naltrexol hydrochloride. Peak intensity is plotted as a function of degrees 2-theta.

Form IX$_S$ of 6-beta-naltrexol hydrochloride is an isopropyl alcohol solvate. The structure of Form IX$_S$ was solved by SCXRD and FIG. 11 shows the simulated pXRD pattern of this form. Form IX$_S$ displayed diffraction peaks above background at 7.419, 10.241, 10.741, 11.563, 11.902, 12.181, 13.303, 14.861, 15.422, 16.018, 16.260, 18.543, 19.159, 19.723, 20.561, 21.262, 21.843, 22.163, 22.821, 23.402, 24.019, 24.300, 25.000, 25.222, 25.801, 26.421, 26.784, 27.084, 27.621, 28.023, 28.621, 28.880, 29.443, 30.164, 31.561, 32.023, 32.582, 33.039, 33.938, 34.363, 34.842, 35.141, 35.640, 36.060, 36.819, 37.480, 37.778, 38.064, 38.540, and 38.862 degrees 2-theta. Form IX$_S$ had predominant peaks at about 7.4, about 11.6, about 13.3, about 16.0, and about 16.3 degrees 2-theta (±0.15 degrees 2-theta).

Example 12

Characterization of Form X$_S$ Crystals

Form X$_S$ of 6-beta-naltrexol hydrochloride is a methyl alcohol solvate. The structure of Form X$_S$ was solved by SCXRD and its simulated pXRD pattern is presented in FIG. 12. Form X$_S$ displayed diffraction peaks above background at 10.778, 11.318, 12.159, 12.903, 13.340, 14.100, 15.642, 16.579, 17.199, 18.959, 19.798, 20.163, 20.558, 20.902, 21.360, 21.641, 22.122, 22.659, 23.379, 24.282, 24.480, 24.943, 25.561, 26.222, 26.859, 27.641, 28.520, 29.119, 29.780, 30.120, 30.363, 30.819, 31.199, 31.403, 32.300, 32.861, 33.381, 34.440, 34.704, 35.401, 36.143, 36.761, 37.220, 37.782, 39.099, 39.521, and 39.821 degrees 2-theta. This form exhibited had predominant peaks at about 12.2, about 12.9, about 13.3, about 15.6, and about 22.7 degrees 2-theta (±0.15 degrees 2-theta).

Example 13

Preparation and Characterization of Form XI$_S$ Crystals

Figure 13:
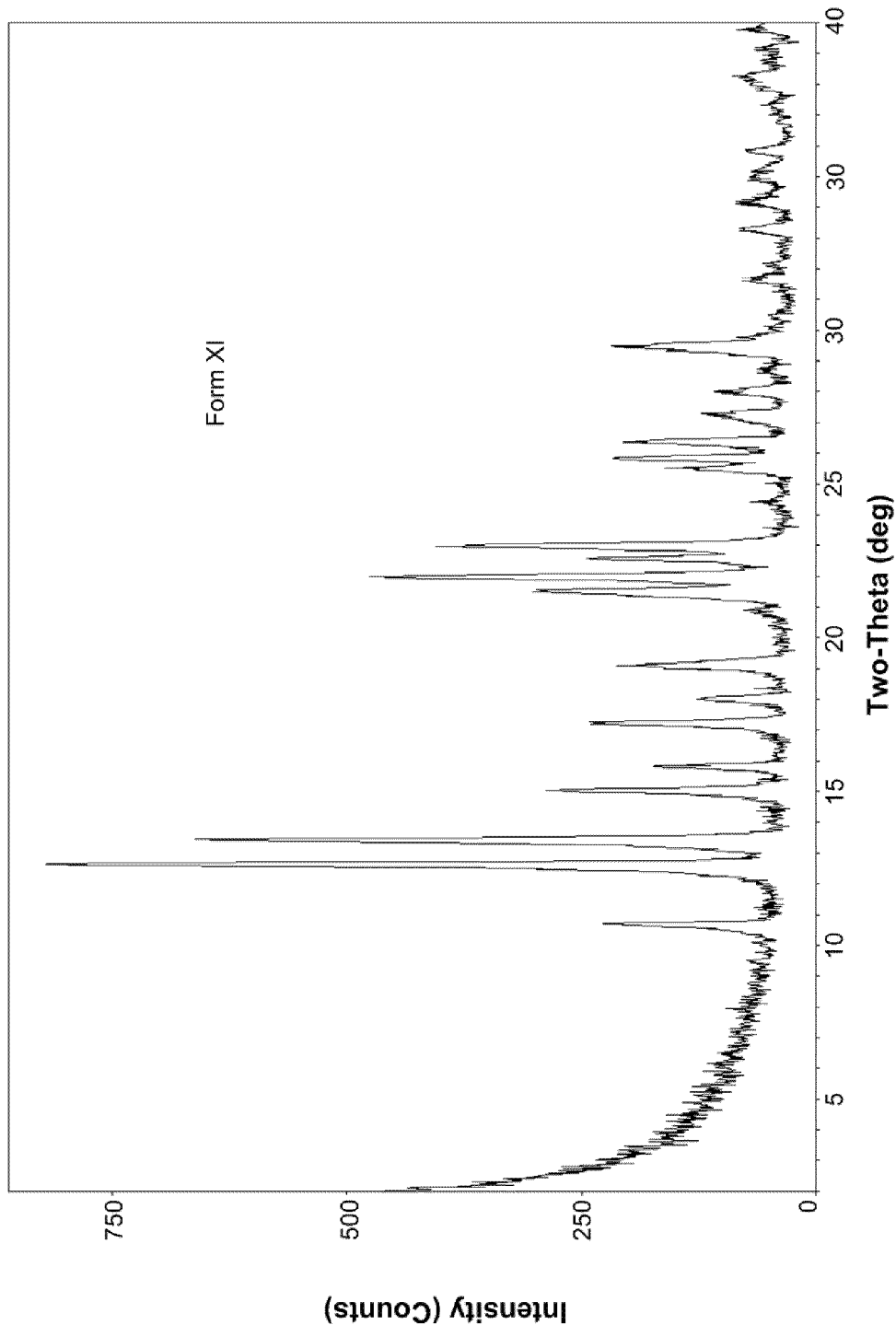
FIG. 13 represents an X-ray powder diffraction pattern of crystalline Form XI of 6-beta-naltrexol hydrochloride. Peak intensity is plotted as a function of degrees 2-theta.

Form XI$_S$ crystals of 6-beta-naltrexol hydrochloride were prepared by sublimation of a small amount of 6-beta-naltrexol hydrochloride. The characteristic pXRD pattern of Form XI$_S$ is shown in FIG. 13. This form exhibited diffraction peaks above background at 7.971, 10.737, 12.681, 13.478, 15.061, 15.844, 17.294, 18.022, 19.141, 21.541, 22.018, 22.618, 23.002, 24.455, 25.559, 25.861, 26.382, 27.161, 27.336, 28.057, 29.518, 29.799, 31.660, 32.216, 33.339, 34.143, 34.992, 35.221, 35.842, 37.359, 37.831, 38.302, and 39.219 degrees 2-theta. Form XI$_S$ had predominant peaks at about 12.7, about 13.5, about 15.1, about 21.5, about 22.0, and about 23.0 degrees 2-theta (±0.15 degrees 2-theta).

DSC traces of Form XI$_S$ showed small, broad endotherms from 25°-125° C., and an endothermic transition at 189°-190° C. TGA traces of Form XI$_S$ exhibited a loss of mass of 0.6-0.7% from 25°-125° C. The observed loss of mass was likely due to the presence of a small amount of Form III$_S$, as this sample was prepared by drying Form III$_S$ under vacuum.

Example 14

Preparation and Characterization of Amorphous Form of Hydrochloride Salt

An amorphous form of 6-beta-naltrexol hydrochloride was prepared by dissolving 6-beta-naltrexol hydrochloride in an alcoholic solution and slowly evaporating the solvent. The alcoholic solutions included 1) water and ethyl alcohol; 2) water and methyl alcohol, and 3) acetone and methyl alcohol (2:1).

Figure 14:
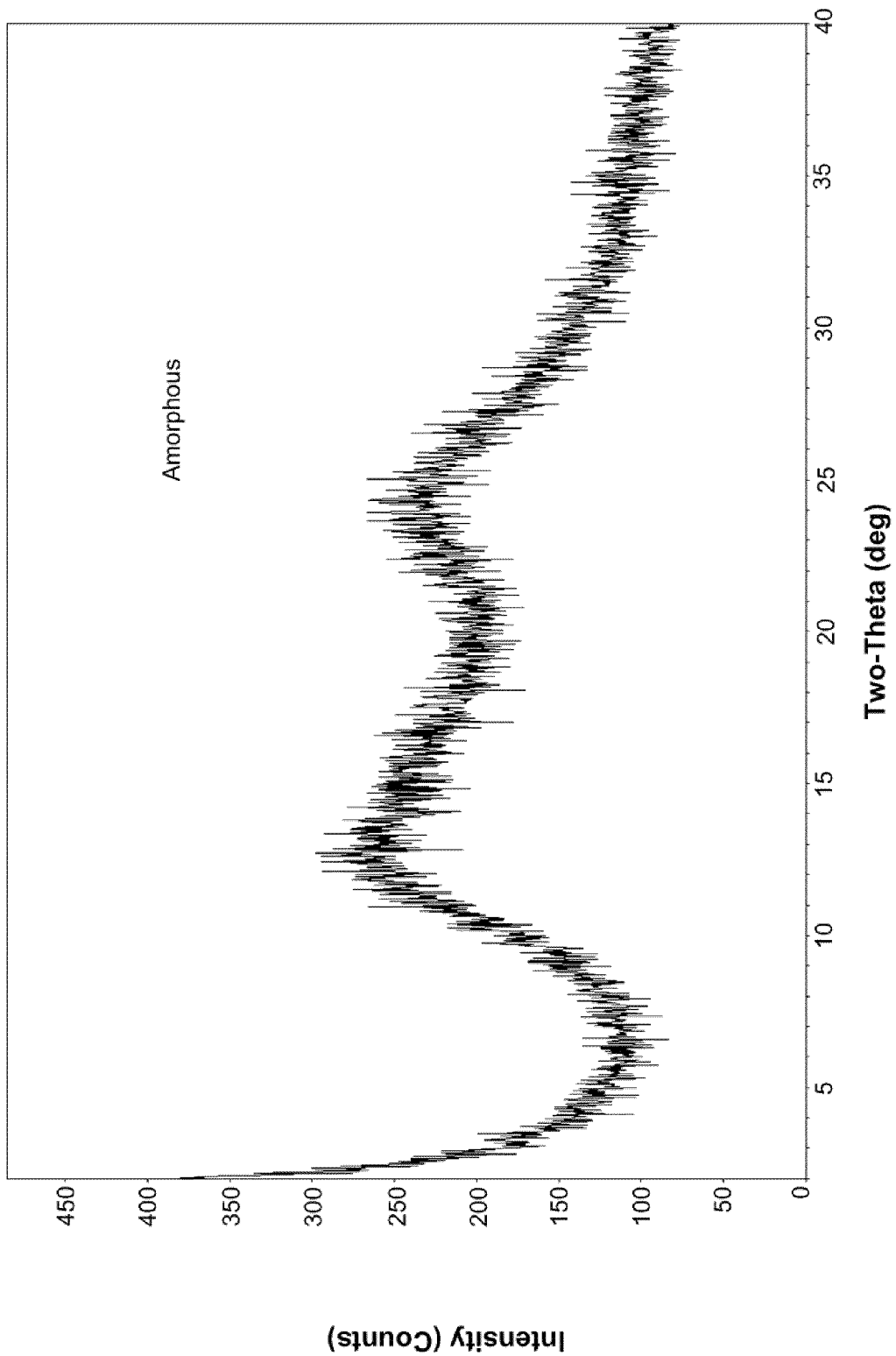
FIG. 14 represents an X-ray powder diffraction pattern of the amorphous Form XII of 6-beta-naltrexol hydrochloride. Peak intensity is plotted as a function of degrees 2-theta, but with a noticeable lack of distinct, sharp peaks.

FIG. 14 presents the pXRD profile of the amorphous form. There were no sharp, distinct diffraction peaks.

What is claimed is:
1. A crystalline form of 6-beta-naltrexol base, morpnhinan-3,6,14-trio,17-(cyclopropvlmethyl)-4,5-epoxy chosen from Form I$_B$ and Form II$_B$, wherein the crystalline form is chosen from the following group:
   i. Form I$_B$, which exhibits an X-ray powder diffraction pattern having characteristic peaks expressed in degrees 2-theta at about 9.8, about 14.0, about 15.9, about 17.2, about 17.7, and about 22.4;
   ii. Form I$_B$, which exhibits a differential scanning calorimetry profile having a endotherm/exotherm from about 75°-125° C. and an endotherm at about 185°-190° C.;
   iii. Form I$_B$, which exhibits a thermogravimetric analysis showing a loss of mass of about 4.0-6.0% from about 75°-160° C.;
   iv. Form II$_B$, which exhibits an X-ray powder diffraction pattern having characteristic peaks expressed in degrees 2-theta at about 10.9, about 15.6, about 16.5, about 17.2, and about 18.7;
   v. Form II$_B$, which exhibits a differential scanning calorimetry profile having an endotherm/exotherm from about 90°-110° C. and an endotherm at about 189°-190° C.; and
   vi. Form II$_B$, which exhibits a thermogravimetric analysis showing a loss of mass of about 0.2-0.3% from about 75°-125° C.

2. A polymorph of 6-beta-naltrexol hydrochloride, morphinan-3,6,14-triol,17-(cyclopropylmethyl)-4,5-epoxy chosen from crystalline Form I$_S$, crystalline Form II$_S$, crystalline Form III$_S$, crystalline Form IV$_S$, crystalline Form V$_S$, crystalline Form VI$_S$, crystalline Form VII$_S$, crystalline Form VIII$_S$, crystalline Form IX$_S$, crystalline Form X$_S$, crystalline Form XI$_S$, and an amorphous form, wherein when the polymorph is a crystalline form, the crystalline form is chosen from the following group:
   i. Form I$_s$, which exhibits an X-ray powder diffraction pattern having characteristic peaks expressed in degrees 2-theta at about 12.8, about 13.9, about 22.7, about 23.3, and about 24.2;
   ii. Form I$_s$, which exhibits a differential scanning calorimetry profile having an endotherm from about 40°-100° C. and an exotherm/endotherm above about 190° C.;
   iii. Form I$_s$, which exhibits a themiogravimetric analysis showing a loss of mass of about 0.2-0.3% from about 40°-100° C.;
   iv. Form II$_s$, which exhibits an X-ray powder diffraction pattern having characteristic peaks expressed in degrees 2-theta at about 7.4, about 11.0, about 11.9, about 14.9, about 15.6, and about 18.8;
   v. Form III$_s$, which exhibits an X-ray powder diffraction pattern having characteristic peaks expressed in degrees 2-theta at about 12.3, about 13.3, about 21.3, about 22.5, about 24.7, and about 33.8;

vi. Form III$_s$, which exhibits a differential scanning calorimetry profile having a first endotherm from about 25°-125° C. and a second endotherm above about 175° C.;
vii. Form III$_s$, which exhibits a thermogravimetric analysis showing a loss of mass of about 7.0-9.0% from about 25°-125° C.;
viii. Form IV$_s$, which exhibits an X-ray powder diffraction pattern having characteristic peaks expressed in degrees 2-theta at about 11.5, about 12.8, about 18.5, about 22.3, about 23.0, and about 23.9;
ix. Form IV$_s$, which exhibits a differential scanning calorimetry profile having an endotherm from about 150°-200° C.;
x. Form IV$_s$, which exhibits a thermogravimetric analysis showing a loss of mass of about 6.0-12.0% from about 150°-200° C.;
xi. Form V$_s$, which exhibits an X-ray powder diffraction pattern having characteristic peaks expressed in degrees 2-theta at about 7.8, about 12.7, about 13.6, about 16.1, about 19.8, and about 23.7;
xii. Form V$_s$, which exhibits a differential scanning calorimetry profile having an endotherm from about 100°-150° C. and an endotherm/exotherm from about 175°-200° C.;
xiii. Form V$_s$, which exhibits a thermogravimetric analysis showing a first loss of mass of about 1.0-1.5% from about 75°-125° C. and a second loss of mass of about 8.0-9.0% from about 150°-180° C.;
xiv. Form VI$_s$, which exhibits an X-ray powder diffraction pattern having characteristic peaks expressed in degrees 2-theta at about 9.7, about 12.2, about 14.4, about 16.0, about 19.4, and about 19.9;
xv. Form VI$_s$, which exhibits a differential scanning calorimetry profile having an endotherm from about 150°-180° C. and an exotherm above about 180° C.;
xvi. Form VI$_s$, which exhibits a thermogravimetric analysis showing a first loss of mass of about 7.0-8.0% from about 150°-200° C. and a second loss of mass of about 1.0-2.0% from about 200°-225° C.;
xvii. Form VII$_s$, which exhibits an X-ray powder diffraction pattern having characteristic peaks expressed in degrees 2-theta at about 12.0, about 13.1, about 21.4, about 22.4, and about 26.2;
xviii. Form VII$_s$, which exhibits a differential scanning calorimetry profile having an first endotherm from about 50°-125° C. and a second endotherm from about 170°-200° C.;
xix. Form VII$_s$, which exhibits a thermogravimetric analysis showing a first loss of mass of about 0.4-0.6% from about 75°-125° C. and a second loss of mass of about 7.0-8.0% from about 150°-200° C.;
xx. Form VIII$_S$, which exhibits an X-ray powder diffraction pattern having characteristic peaks expressed in degrees 2-theta at about 11.7, about 12.9, about 13.1, about 18.9, and about 24.4;
xxi. Form IX$_S$, which exhibits an X-ray powder diffraction pattern having characteristic peaks expressed in degrees 2-theta at about 7.4, about 11.6, about 13.3, about 16.0, and about 16.3;
xxii. Form X$_S$, which exhibits an X-ray powder diffraction pattern having characteristic peaks expressed in degrees 2-theta at about 12.2, about 12.9, about 13.3, about 15.6, and about 22.7;
xxiii. Form XI$_S$, which exhibits an X-ray powder diffraction pattern having characteristic peaks expressed in degrees 2-theta at about 12.7, about 13.5, about 15.1, about 21.5, about 22.0, and about 23.0;
xxiv. Form XI$_S$, which exhibits a differential scanning calorimetry profile having a first endotherm from about 25°-125° C. and a second endotherm at about 189°-190° C.; and
xxv. Form XI$_S$ is, which exhibits a thermogravimetric analysis showing a loss of mass of about 0.6-0.7% from about 25°-125° C.

3. The polymorph of claim 2, wherein the polymorph is the amorphous form and lacks characteristic peaks as determined by X-ray powder diffraction spectrometry.

4. A pharmaceutical composition, the composition comprising at least one crystalline form of 6-beta-naltrexol base, morphinan -3,6,14-triol,17-(cyclopropylmethyl)-4,5-epoxy, of calim 2 and at least one pharmaceutically acceptable excipient, wherein the crystalline form of 6-beta-naltrexol base is chosen from Form I$_B$, Form II$_B$ and combinations thereof wherein the crystalline Form I$_B$ exhibits an X-ray powder diffraction pattern having characteristic peaks expressed in degrees 2-theta at 9.8, about 14.0, about 15.9, about 17.2, about 17.7, and about 22.4; a differential scanning calorimetry profile having a endotherm/exotherm at about 75°-125° C. and an endotherm at about 185°-190° C.; and a thermogravimetric analysis showing a loss of mass of about 4.0-6.0% from about 75°-160° C.

5. The pharmaceutical composition of claim 4, wherein the crystalline Form II$_B$ exhibits an X-ray powder diffraction pattern having characteristic peaks expressed in degrees 2-theta at about 10.9, about 15.6, about 16.5, about 17.2, and about 18.7; a differential scanning calorimetry profile having an endotherm/exotherm at about 90°-110° C. and an endotherm at about 189°-190° C.; and a thermogravimetric analysis showing a loss of mass of about 0.2-0.3% from about 75°-125° C.

6. A pharmaceutical composition, the composition comprising at least one polymorph of 6-beta-naltrexol hydrochloride, morphinan-3, 6,14-triol, 17-(cyclopropylmethy)-4,5-epoxy, and at least one pharmaceutically acceptable excipient, wherein the polymorph of 6-beta-naltrexol hydrochloride is chosen from crystalline Form I$_s$, crystalline Form II$_s$, crystalline Form III$_s$, crystalline Form IV$_s$ crystalline Form V$_s$, crystalline Form VI$_s$, crystalline Form VII$_s$, crystalline Form VIII$_s$, crystalline Form IX$_s$, crystalline Form X$_s$, crystalline Form XI$_s$, an amorphous form, and combinations thereof, wherein the crystalline form is chosen from the following group:
i. Form I$_s$, which exhibits an X-ray powder diffraction pattern having characteristic peaks expressed in degrees 2-theta at about 12.8, about 13.9, about 22.7, about 23.3, and about 24.2; a differential scanning calorimetry profile having an endotherm from about 40°-100° C. and an exotherm/endotherm above about 190° C.; and a thermogravimetric analysis showing a loss of mass of about 0.2-0.3% from about 40°-100° C.;
ii. Form II$_s$, which exhibits an X-ray powder diffraction pattern having characteristic peaks expressed in degrees 2-theta at about 7.4, about 11.0, about 11.9, about 14.9, about 15.6, and about 18.8;
iii. Form III$_s$, which exhibits an X-ray powder diffraction pattern having characteristic peaks expressed in degrees 2-theta at about 12.3, about 13.3, about 21.3, about 22.5, about 24.7, and about 38.8; a differential scanning calorimetry profile having a first endotherm from about 25°-125° C. and a second endotherm above about 175° C.; and a thermogravimetric analysis showing a loss of mass of about 7.0-9.0% from about 25°-125° C.;
iv. Form IV$_s$, which exhibits an X-ray powder diffraction pattern having characteristic peaks expressed in degrees 2-theta at about 11.5, about 12.8, about 18.5, about 22.3, about 23.0, and about 23.9; a differential scanning calorimetry profile having an endotherm from about 150°-200° C.; and a thermogravimetric analysis showing a loss of mass of about 6.0-12.0% from about 150°-200° C.;

v. Form $V_S$, which exhibits an X-ray powder diffraction pattern having characteristic peaks expressed in degrees 2-theta at about 7.8, about 12.7, about 13.6, about 16.1, about 19.8, and about 23.7; a differential scanning calorimetry profile having an endotherm from about 100°-150° C. and an endotherm/exotherm from about 175°-200° C.; and a thermogravimetric analysis showing a first loss of mass of about 1.0-1.5% from about 75-125° C. and a second loss of mass of about 8.0-9.0% from about 150°-180° C.;

vi. Form $VI_S$, which exhibits an X-ray powder diffraction pattern having characteristic peaks expressed in degrees 2-theta at about 9.7, about 12.2, about 14.4, about 16.0, about 19.4, and about 19.9; a differential scanning calorimetry profile having an endotherm from about 150°-180° C. and an exotherm above about 180° C.; and a thermogravimetric analysis showing a first loss of mass of about 7.0-8.0% from about 150°-200° C. and a second loss of mass of about 1.0-2.0% from about 200°-225° C.;

vii. Form $VII_S$, which exhibits an X-ray powder diffraction pattern having characteristic peaks expressed in degrees 2-theta at about 12.0, about 13.1, about 21.4, about 22.4, and about 26.2; a differential scanning calorimetry profile having an first endotherm from about 50°-125° C. and a second endotherm from about 170°-200° C.; and a first loss of mass of about 0.4-0.6% from about 75°-125° C. and a second loss of mass of about 7.0-8.0% from about 150°-200° C.;

viii. Form $VIII_S$, which exhibits an X-ray powder diffraction pattern having characteristic peaks expressed in degrees 2-theta at about 11.7, about 12.9, about 13.1, about 18.9, and about 24.4;

ix. Form $IX_S$, which exhibits an X-ray powder diffraction pattern having characteristic peaks expressed in degrees 2-theta at about 7.4, about 11.6, about 13.3, about 16.0, and about 16.3;

x. Form $X_S$, which exhibits an X-ray powder diffraction pattern having characteristic peaks expressed in degrees 2-theta at about 12.2, about 12.9, about 13.3, about 15.6, and about 22.7; and xi. Form $XI_S$, which exhibits an X-ray powder diffraction pattern having characteristic peaks expressed in degrees 2-theta at about 12.7, about 13.5, about 15.1, about 21.5, about 22.0, and about 23.0; a differential scanning calorimetry profile having a first endotherm from about 25°-125° C. and a second endotherm at about 189°-190° C.; and a thermogravimetric analysis showing a loss of mass of about 0.6-0.7% from about 25°-125° C.

7. A process for preparing a substantially pure crystalline Form $II_B$ form of 6-beta-naltrexol base, mornorphinan-3,6,14-triol,17-(cyclopropylmethyl)-4,5-epoxy, the process comprising:

i. contacting 6-beta-naltrexol base at an elevated temperature with a solvent comprising isopropyl alcohol to form a saturated or a near saturated solution; and ii. cooling the solution to form crystals of the substantially pure crystalline Form $II_B$ of 6-beta-naltrexol base, wherein the crystalline Form $II_B$ exhibits an X-ray powder diffraction pattern having characteristic peaks expressed in degrees 2-theta at about 10.9, about 15.6, about 16.5, about 17.2, and about 18.7; a differential scanning calorimetry profile having an endotherm/exotherm at about 90°-110° C. and an endotherm at about 189°-190° C.; and a thermogravimetric analysis showing a loss of mass of about 0.2-0.3% from about 75-125° C.

* * * * *